United States Patent
Islam et al.

(10) Patent No.: US 7,812,251 B2
(45) Date of Patent: Oct. 12, 2010

(54) PHOTOSENSITIZING TRANSITION METAL COMPLEX AND ITS USE FOR PHOTOVOLTAIC CELL

(75) Inventors: Ashraful Islam, Yamatotakada (JP); Liyuan Han, Nara (JP); Atsushi Fukui, Kashiba (JP)

(73) Assignee: Sharp Kabushiki Kaisha, Osaka (JP)

( * ) Notice: Subject to any disclaimer, the term of this patent is extended or adjusted under 35 U.S.C. 154(b) by 1618 days.

(21) Appl. No.: 10/964,745

(22) Filed: Oct. 15, 2004

(65) Prior Publication Data

US 2005/0081911 A1  Apr. 21, 2005

(30) Foreign Application Priority Data

Oct. 17, 2003  (JP)  .............................. 2003-358266
Dec. 5, 2003  (JP)  .............................. 2003-407877

(51) Int. Cl.
*H01L 31/00*  (2006.01)
*H01G 9/20*  (2006.01)
*C07F 15/00*  (2006.01)
*H01M 14/00*  (2006.01)
*H01L 31/04*  (2006.01)

(52) U.S. Cl. ........................... 136/263; 136/252; 546/2; 546/21; 546/257; 546/258; 546/263; 546/272.4; 546/273.4; 546/8; 546/10; 429/11; 429/212; 429/213; 257/40; 257/428; 257/431; 257/439; 556/136; 556/137; 544/225

(58) Field of Classification Search .................... 546/21, 546/2, 8, 10, 257, 258, 263, 272.4, 273.4; 136/256, 263, 252; 429/11, 212, 213; 257/40, 257/428, 431, 439; 556/136, 137; 544/255
See application file for complete search history.

(56) References Cited

U.S. PATENT DOCUMENTS 5,789,592 A * 8/1998 Gratzel et al. .................. 546/21
(Continued)

FOREIGN PATENT DOCUMENTS

JP  2664194  6/1997
(Continued)

OTHER PUBLICATIONS

Raffard et al. ("Biomimetic Catalysis of Catechol Cleavage by O2 in Organic Solvents-Role of Accessibility of O2 to Fe(III) in 2,11-Diaza[3,3](2,6)pyridinophane-Type Catalyst", European Journal of Inorganic Chemistry, (2001), pp. 2249-2254).*

(Continued)

*Primary Examiner*—Alexa D Neckel
*Assistant Examiner*—Golam Mowla
(74) *Attorney, Agent, or Firm*—Nixon & Vanderhye P.C.

(57) ABSTRACT

A photosensitizing transition metal complex of the formula (Ia) $MLY^1$, (Ib) $MLX_3$ (Ic) $MLY^2X$, (Id) $MLY^3X$ or (Ie) $MLY^4X$ in which M is a transition metal selected from ruthenium, osmium, iron, rhenium and technetium, preferably ruthenium or osmium. X is a co-ligand independently selected from NCS—, Cl—, Br—, I—, CN—, $H_2O$; pyridine unsubstituted or substituted by at least one group selected from vinyl, primary, secondary or tertiary amine, OH and $C_{1-30}$ alkyl, preferably NSC and CN—; L is a tridentate polypyridine ligand, carrying at least one carboxylic, phosphoric acid or a chelating group and one substituted or unsubstituted alkyl group having 1 to 50 carbon atoms, substituted or unsubstituted alkylamide group having 2 to 30 carbon atoms or substituted or unsubstituted aralkyl group having 7 to 50 carbon atoms. A dye-sensitized electrode includes a substrate having an electrically conductive surface, an oxide semiconductor film formed on the conductive surface, and the above sensitizer of formula (Ia), (Ib), (Ic), (Id) or (Ie) as specified above, supported on the film. A solar cell includes the above electrode, a counter electrode, and an electrolyte deposited there between.

5 Claims, 1 Drawing Sheet

U.S. PATENT DOCUMENTS

| | | | |
|---|---|---|---|
| 6,245,988 B1 * | 6/2001 | Gratzel et al. | 136/263 |
| 6,291,763 B1 * | 9/2001 | Nakamura | 136/256 |
| 6,500,975 B1 * | 12/2002 | Schwab et al. | 556/22 |
| 6,562,973 B1 * | 5/2003 | Liu | 546/12 |
| 6,911,595 B2 * | 6/2005 | Yoshikawa et al. | 136/263 |
| 2003/0069374 A1 * | 4/2003 | Grubbs et al. | 526/171 |
| 2003/0096997 A1 * | 5/2003 | Mao et al. | 546/2 |
| 2003/0144513 A1 * | 7/2003 | Islam et al. | 546/2 |

FOREIGN PATENT DOCUMENTS

| | | |
|---|---|---|
| JP | 2001-203005 | 7/2001 |
| JP | 2001-226607 | 8/2001 |
| JP | 2001-253894 | 9/2001 |
| JP | 2003-212851 | 7/2003 |

OTHER PUBLICATIONS

Sellmann et al., "Transition Metal Complexes with Sulfur Ligands. 136.1 Enforced Trans Coordination of Thiolate Donors in Electron Rich Iron . . . ", Inorg. Chem., 38 (23), 5314-5322, 1999.*

Babich et al., "99mTc-labeled chemotactic peptides: influence of coligand on distribution of molecular species and infection imaging properties. Synthesis and structural characterization of model complexes with the {Re($\eta$2-HNNC5H4N)($\eta$1-NNC5H4N)} core", Inorganica Chimica Acta, vol. 309, Issues 1-2, Nov. 20, 2000, pp. 123-136.*

Nishiyama et al., Chem. Commun., 1997, pp. 1863-1864.*

Islam, A. et al., "Efficient panchromatic sensitization of nancrystalline TiO$_2$ films by $\beta$-diketonato ruthenium polypyridyl complexes", *New J. Chem.*, 26:966-968 (2002).

* cited by examiner

PHOTOSENSITIZING TRANSITION METAL COMPLEX AND ITS USE FOR PHOTOVOLTAIC CELL

CROSS-REFERENCE TO RELATED APPLICATIONS

This application is related to Japanese applications Nos. 2003-358266 and 2003-407877, filed on 17 Oct., 2003 and 5 Dec., 2003 whose priorities are claimed under 35 USC §119, the disclosures of which are incorporated by reference in their entirety.

BACKGROUND OF THE INVENTION

1. Field of the Invention

The invention relates to new photosensitizing transition metal complex and its use for photovoltaic cell such as solar cell.

2. Description of the Related Art

Photosensitive dyes are coated on metal oxide films rendering a device as solar cell effective in the conversion of visible light to electric energy. In this solar cell, a monolayer of dye is attached to the surface of nanocrystalline metal dioxide film. Photoexcitation of the dye results in the injection of an electron into the conduction band of the metal oxide. The original state of the dye is subsequently restored by electron donation from a redox system, such as iodide/triiodide couple. Molecular design of ruthenium polypyridyl photosensitizers for nanocrystalline $TiO_2$ film in solar cell that can absorb visible lights of all colors presents a challenging task. The dyes should have suitable ground- and excited state redox properties so that the two key electron transfer steps (charge injection and regeneration of the dye) occur efficiently.

The most efficient transition metal complexes employed so far in the solar cell are Ru(II) polypyridyl complexes because of their intense charge-transfer (CT) absorption in the whole visible range, moderately intense emission with fairly long lifetime in fluid solution at ambient temperature, high quantum yield for the formation of the lowest CT excited state, and redox reactivity and ease of tunability of redox properties. So far, the most successful photosensitizers employed in solar cell are Ru(4,4'-dicarboxy-2,2'-bipyridine)$_2$(NCS)$_2$ and Ru(4,4',4"-tricarboxy-2,2':6',2"-terpyridine)(NCS)$_3$. The role of the monodentate thiocyanato ligands is to tune the spectral and redox properties of the photosensitizers by destabilization of the metal $t_{2g}$ orbital.

The presence of monodentate donor ligands (NCS—) can undergo ligand photosubstitution or photodegradation reaction via population of an upper lying ligand field excited state and these processes can be reduced by multidentate ligands.

As relevant prior arts are mentioned U.S. Pat. No. 6,245,988, U.S. Pat. No. 5,789,592, Japanese Patent Kokai No. 2003-212851 and New J. Chem. 26 (2002) 966-968.

SUMMARY OF THE INVENTION

The present invention aims to provide a new series of photochemically stable amphiphilic transition metal complexes to improve the efficiency, durability and stability of dye sensitized nanocrystalline solar cell.

According to the invention, there is provided photosensitizing transition metal complexes represented by the formulae (Ia), (Ib), (Ic), (Id) and (Ie)

$$MLY^1 \quad (Ia)$$

$$MLX_3 \quad (Ib)$$

$$MLY^2X \quad (Ic)$$

$$MLY^3X \quad (Id) \text{ and}$$

$$MLY^4X \quad (Ie)$$

In the formulae, M is a transition metal selected from Ru(II), Os(II), Fe(II), Re(I) and Tc(I);

L is a polypyridine ligand having the general formula (II):

(II)

[Structure of tripyridine ligand with substituents $A_1$, $A_2$, $A_3$]

wherein at least one of $A_1$, $A_2$ and $A_3$ is an anchoring group selected from —COOH, —COON($C_4H_9$)$_4$, —PO(OH)$_2$, —PO(OR$_1$)$_2$ (where $R_1$ is an alkyl group having 1 to 30 carbon atoms), —CO(NHOH), and when there is the remaining $A_1$, $A_2$ and $A_3$ being not said anchoring group, it may be a hydrogen atom, an alkyl group having 1 to 50 carbon atoms, an alkylamide group having 2 to 50 carbon atoms or an aralkyl group having 7 to 50 carbon atoms.

Preferably, $A_1$, $A_2$ and $A_3$ contain at least one anchoring group as mentioned above and at least one group selected from the alkyl, alkylamide and aralkyl groups.

X is a ligand selected from NCS—, Cl—, Br—, I—, CN—, NCO—, $H_2O$ or pyridine group which may be substituted by vinyl, primary, secondary or tertiary amino, alkylthio or arylthio, hydroxyl or $C_{1-30}$ alkyl.

$Y^1$ is a group selected from the formulae (IIIa) to (IIId):

(III a)

[Structure with $H_2N$, $HN$, $H_2N$ groups]

(III b)

[Structure with pyridine ring and $R_3$ substituent, with ether linkages]

(III c)

[Structure with pyridine ring, $R_3$ substituent, and $H_2N$ groups]

-continued

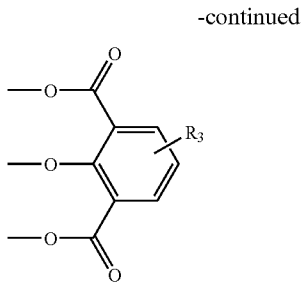
(III d)

where R₃ is an alkyl group having 1 to 50 carbon atoms, an alkoxyalkyl group having 2 to 30 carbon atoms, an aminoalkyl group having 1 to 30 carbon atoms, an alkoxycarbonyl group having 2 to 20 carbon atoms, an alkylamide group having 2 to 30 carbon atoms, a cyano group or a hydrogen atom.

$Y^2$ is a group having the general formula (IVa-1):

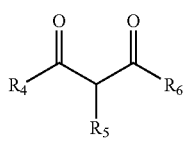
(IV a-1)

where $R_4$, $R_5$ and $R_6$ are independently an alkyl group having 1 to 20 carbon atoms, an alkoxyalkyl group having 2 to 12 carbon atoms, an aminoalkyl group having 1 to 12 carbon atoms, an alkoxycarbonyl group having 2 to 6 carbon atoms, an alkylamide group having 2 to 30 carbon atoms, a perfluoroalkyl group having 1 to 12 carbon atoms, an alkoxy group having 1 to 6 carbon atoms, an aryl group, cyano group, hydroxyl group, nitro group, amino group, trifluoro group, halogen atom or hydrogen atom.

$Y^3$ is a group having the formula (IVa-2):

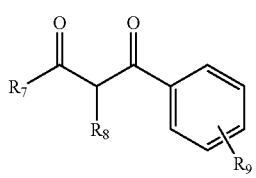
(IV a-2)

where $R_7$ is a trifluoro or perfluoroalkyl group having 1 to 12 carbon atoms, $R_8$ and $R_9$ are independently the same meanings as $R_5$ and $R_6$ of the formula (IVa-1).

$Y^4$ is a group selected from the formulae (IVb-1 to 3), (IVc-1 to 4), (IVd-1 to 8) and (IVe-1 or 2):

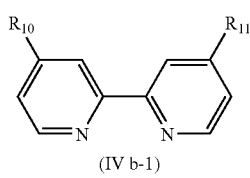

Formula IVb (IV b-1)

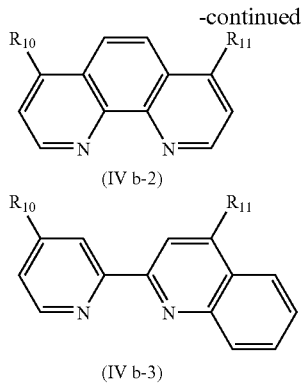
(IV b-2)

(IV b-3)

Formula IVc

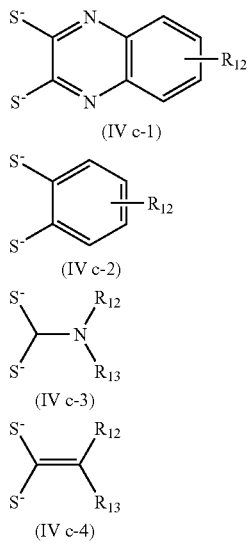
(IV c-1)

(IV c-2)

(IV c-3)

(IV c-4)

Formula IVd

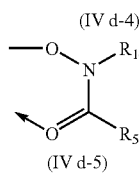
(IV d-1)

(IV d-2)

(IV d-3)

(IV d-4)

(IV d-5)

-continued

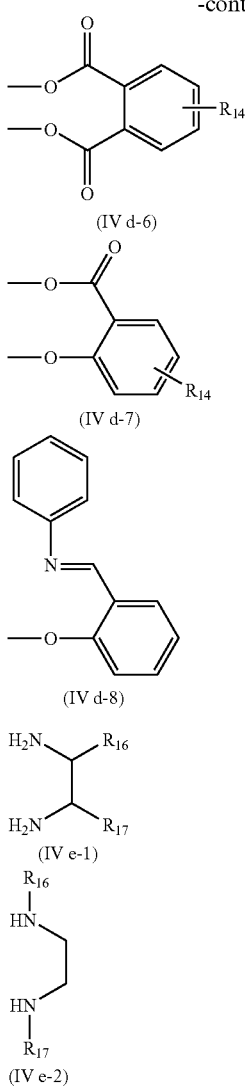

(IV d-6)

(IV d-7)

(IV d-8)

(IV e-1)

(IV e-2)

where $R_{10}$, $R_{11}$, $R_{12}$, $R_{13}$, $R_{14}$, $R_{15}$, $R_{16}$ and $R_{17}$ are the same or different an alkyl group having 1 to 20 carbon atoms, an alkoxyalkyl group having 2 to 12 carbon atoms, an perfluoroalkyl group having 2 to 12 carbon atoms, an alkylamide group having 2 to 12 carbon atoms, an aminoalkyl group having 1 to 12 carbon atoms, an alkoxycarbonyl group having 2 to 6 carbon atoms, an alkoxy group having 1 to 6 carbon atoms, an aryl group, cyano group, hydroxyl group, nitro group, amino group, trifluoro group, halogen atom or hydrogen atom.

The present invention further provides a photovoltaic cell comprising a support, a conductive layer formed on the support, and a porous semiconductor layer formed on the conductive layer, wherein the porous semiconductor layer carries a photosensitizing transition metal complex as defined above.

These and other objects of the present application will become more readily apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE PREFERRED EMBODIMENTS OF THE INVENTION

Figure 1:
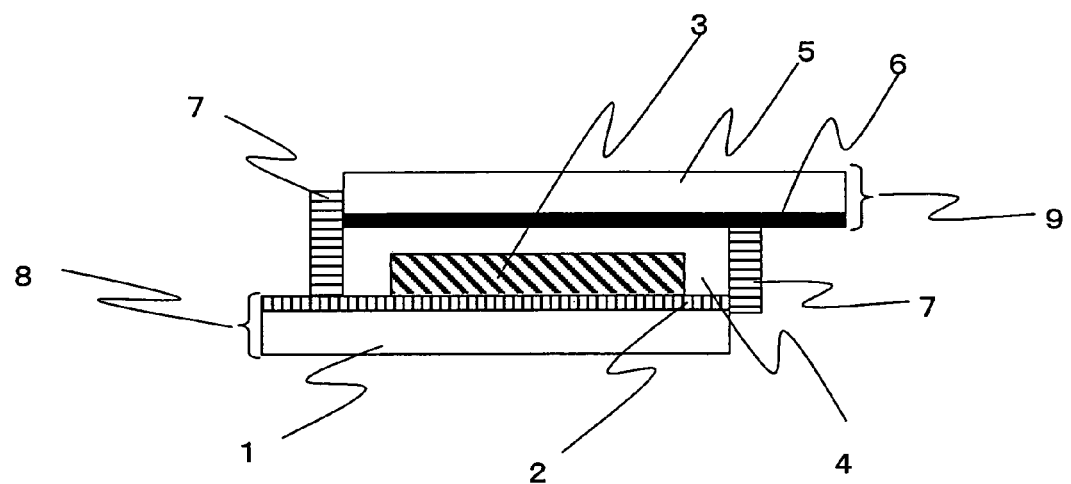
FIG. 1 is a diagrammatic sectional view showing the structure of a solar cell constructed in the present invention.

In the formulae (Ia) to (Ie), the symbols or groups will be explained in detail.

The transition metal for M is preferred to be Ru(II) and Os(II).

The ligand for X is preferred to be NCS— and CN—.

The polypyridine ligand for the general formula (II) is preferred to be those of the subformula (IIa):

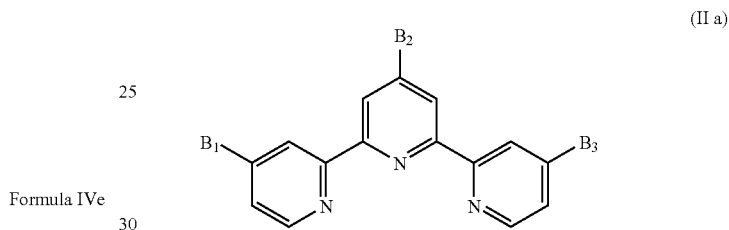

(II a)

where $B_1$, $B_2$ and $B_3$ are H, —COOH, —COON$(C_4H_9)_4$ or —PO(OH)$_2$ provided that at least one of $B_1$, $B_2$ and $B_3$ is different from hydrogen atom; and subformula (IIb):

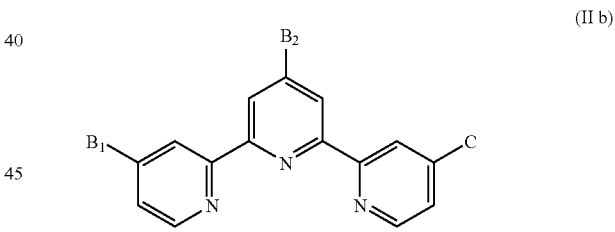

(II b)

where $B_1$ and $B_2$ are, the same or different, a hydrogen atom, —COOH, —COON$(C_4H_9)_4$, —PO(OH)$_2$, provided that any one of $B_1$ and $B_2$ is different from a hydrogen atom, and C is an alkyl group having 6 to 30 carbon atoms.

The alkyl moiety used in the alkyl group, the alkylamide group, the aralkyl group, the alkoxyalkyl group, the aminoalkyl group, the alkoxycarbonyl group, the alkylthio group, the tri or perfluoro alkyl may be either straight chain or branched chain and further may be optionally substituted by any group(s) which does not interfere the property for photosensitizer.

The aryl moiety used in the aralkyl group may be optionally substituted by any group(s) which does not interfere the property for photosensitizer.

Preferred polypyridine ligands for L which can contribute for the best to increase the efficiency and stability of photovoltaic cell are those having at least one anchoring group of —COOH and —PO(OH)$_2$, specifically as mentioned below.

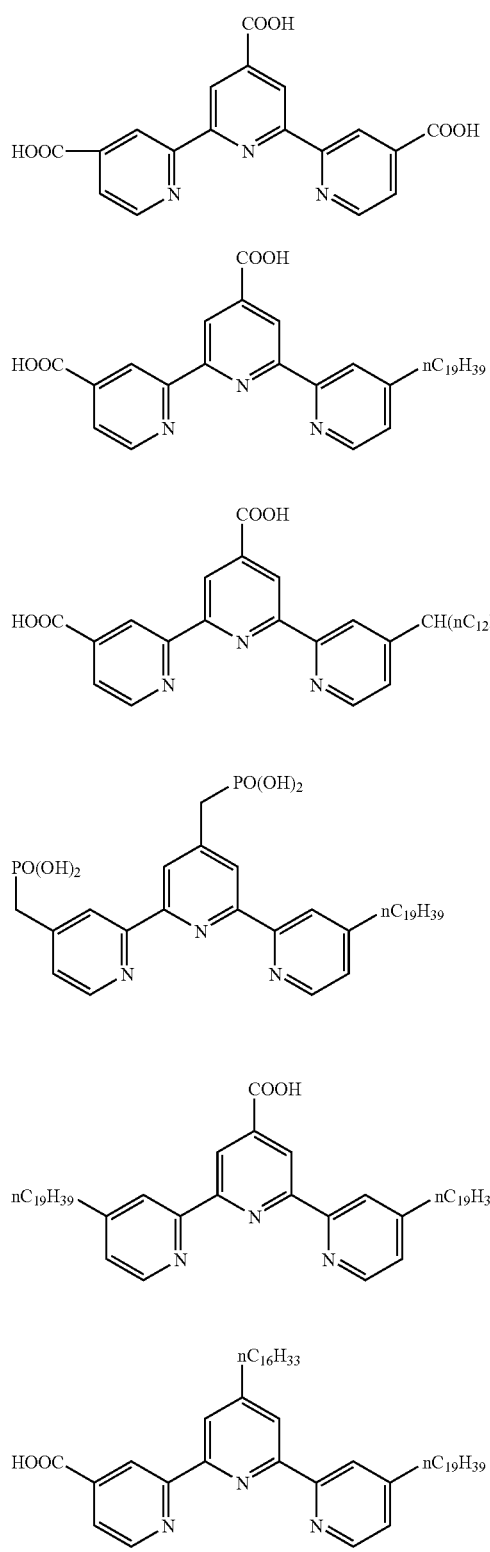

(1)
(2)
(3)
(4)
(5)
(6)

Specifically, preferred illustrative examples of the photo-sensitizing transition metal complexes of the general formula (Ia) are ruthenium complexes as shown by Complex types 1 to 4 in Table 1 to 4.

TABLE 1

Complex type 1:

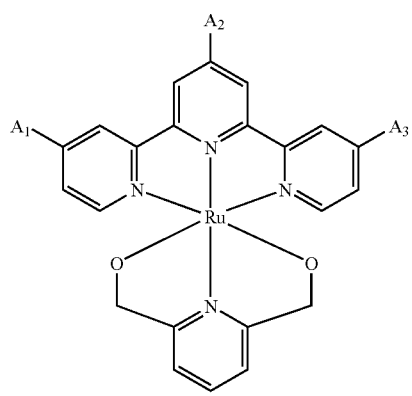

| Complex type No | $A_1$ | $A_2$ | $A_3$ |
|---|---|---|---|
| 1a | COOH | COOH | COOH |
| 1b | COOH | COOH | $nC_{19}H_{39}$ |
| 1c | COOH | COOH | $nCH(C_{12}H_{25})_2$ |
| 1d | $nC_{19}H_{39}$ | COOH | $nC_{19}H_{39}$ |
| 1e | COOH | $nC_{16}H_{33}$ | $nC_{19}H_{39}$ |
| 1f | COOH | COOH | $nC_{17}H_{35}$ |
| 1g | COOH | COOH | $nCH(C_8H_{17})_2$ |
| 1h | $nC_{17}H_{35}$ | COOH | $nC_{17}H_{35}$ |
| 1i | COOH | $nC_8H_{17}$ | $nC_9H_{19}$ |

TABLE 2

Complex type 2:

| Complex type No | $A_1$ | $A_2$ | $A_3$ |
|---|---|---|---|
| 2a | COOH | COOH | COOH |
| 2b | COOH | COOH | $nC_{19}H_{39}$ |
| 2c | COOH | COOH | $nCH(C_{12}H_{25})_2$ |
| 2d | $nC_{19}H_{39}$ | COOH | $nC_{19}H_{39}$ |
| 2e | COOH | $nC_{16}H_{33}$ | $nC_{19}H_{39}$ |

TABLE 3

Complex type 3:

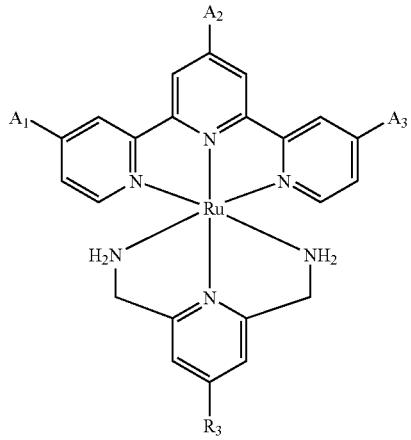

| Complex type No | $A_1$ | $A_2$ | $A_3$ | $R_3$ |
|---|---|---|---|---|
| 3a | COOH | COOH | COOH | H |
| 3b | COOH | COOH | COOH | $nC_{16}H_{33}$ |
| 3c | COOH | COOH | $nC_{19}H_{39}$ | H |
| 3d | COOH | COOH | $nC_{19}H_{39}$ | $nC_{16}H_{33}$ |
| 3e | COOH | COOH | $nCH(C_{12}H_{25})_2$ | H |
| 3f | $nC_{19}H_{39}$ | COOH | $nC_{19}H_{39}$ | H |
| 3g | COOH | $nC_{16}H_{33}$ | $nC_{19}H_{39}$ | H |
| 3h | COOH | COOH | $nC_{17}H_{35}$ | H |
| 3i | COOH | COOH | $nCH(C_8H_{17})_2$ | H |
| 3j | $nC_{17}H_{35}$ | COOH | $nC_{17}H_{35}$ | H |
| 3k | COOH | $NC_8H_{17}$ | $NC_9H_{19}$ | H |

TABLE 4

Complex type 4:

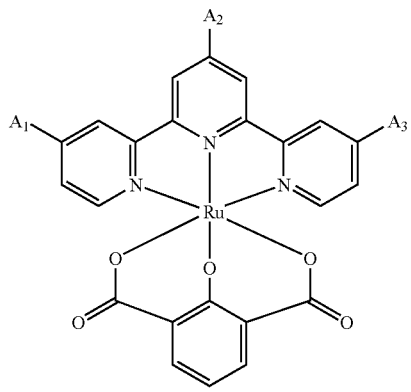

| Complex type No | $A_1$ | $A_2$ | $A_3$ |
|---|---|---|---|
| 4a | COOH | COOH | COOH |
| 4b | COOH | COOH | $NC_{19}H_{39}$ |
| 4c | COOH | COOH | $nCH(C_{12}H_{25})_2$ |
| 4d | $nC_{19}H_{39}$ | COOH | $NC_{19}H_{39}$ |
| 4e | COOH | $nC_{16}H_{33}$ | $NC_{19}H_{39}$ |

Specifically, preferred illustrative examples of the photosensitizing transition metal complex of the general formula (Ib) are ruthenium complexes as shown by Complex type 5 in Table 5.

TABLE 5

Complex type 5:

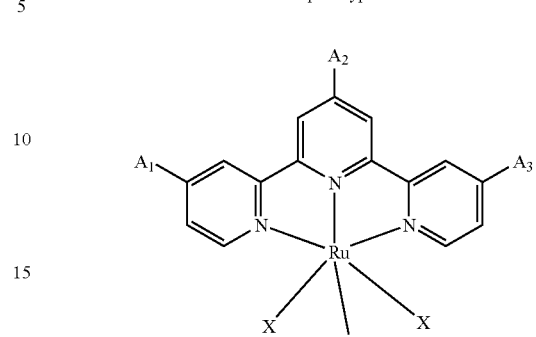

| Complex type No | $A_1$ | $A_2$ | $A_3$ | X |
|---|---|---|---|---|
| 5a | COOH | COOH | $nC_{19}H_{39}$ | NSC— |
| 5b | COOH | COOH | $nCH(C_{12}H_{25})_2$ | NSC— |
| 5c | $nC_{19}H_{39}$ | COOH | $nC_{19}H_{39}$ | NSC— |
| 5d | COOH | $nC_{16}H_{33}$ | $nC_{19}H_{39}$ | NSC— |

Specifically, preferred illustrative examples of the photosensitizing transition metal complex of the general formula (Ic) are ruthenium complexes as shown by Complex type 6 in Table 6 and 7.

TABLE 6

Complex type 6:

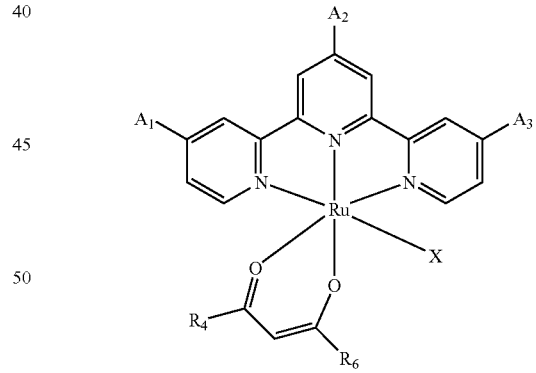

| $R_4$ | $R_5$ | $R_6$ | No | $R_4$ | $R_5$ | $R_6$ | No |
|---|---|---|---|---|---|---|---|
| $CH_3$ | H | $CH_3$ | 1 | $CF_3$ | H | $CH_3$ | 7 |
| $CH_3$ | CH3 | $CH_3$ | 2 | $CF_3$ | H | $CH_2CN$ | 8 |
| t-Bu | H | t-Bu | 3 | $CF_3$ | H | $CF_3$ | 9 |
| Ph | H | $CH_3$ | 4 | $CF_3$ | H | $R_1$ | 10 |
| Ph | H | Ph | 5 | $CF_3$ | H | $CF_3$—$CF_2$ | 11 |
| $CH_3$ | H | $R_1$ | 6 | $CF_3$ | H | Ph | 12 |

$R_1$ being selected from $C_{1-30}$ alkyl

TABLE 7

| Complex type No | $A_1$ | $A_2$ | $A_3$ | $R_4$ | $R_6$ | X |
|---|---|---|---|---|---|---|
| 6a | COOH | COOH | $nC_{19}H_{39}$ | $CF_3$ | $CH_3$ | NSC— |
| 6b | COOH | COOH | $nCH(C_{12}H_{25})_2$ | $CF_3$ | $CH_3$ | NSC— |
| 6c | $nC_{19}H_{39}$ | COOH | $nC_{19}H_{39}$ | $CF_3$ | $CH_3$ | NSC— |
| 6d | COOH | $nC_{16}H_{33}$ | $nC_{19}H_{39}$ | $CF_3$ | $CH_3$ | NSC— |
| 6e | COOH | COOH | $NC_{17}H_{35}$ | $CF_3$ | $CH_3$ | NSC— |
| 6f | COOH | COOH | $nCH(C_8H_{17})_2$ | $CF_3$ | $CH_3$ | NSC— |
| 6g | $nC_{17}H_{35}$ | COOH | $nC_{17}H_{35}$ | $CF_3$ | $CH_3$ | NSC— |
| 6h | COOH | $NC_8H_{17}$ | $NC_9H_{19}$ | $CF_3$ | $CH_3$ | NSC— |

Specifically, preferred illustrative examples of the photosensitizing transition metal complex of the general formula (Id) are ruthenium complexes as shown by Complex type 7 in Table 8 and 9.

TABLE 8

Complex type 7:

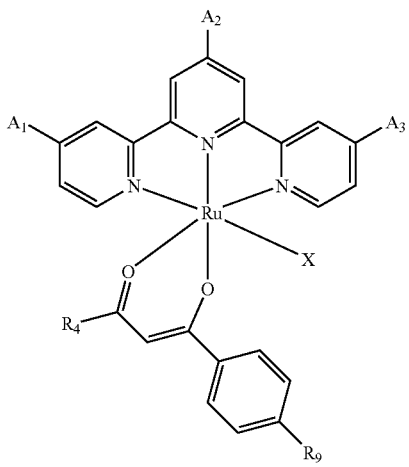

| $R_7$ | $R_8$ | $R_9$ | No | $R_7$ | $R_8$ | $R_9$ | No |
|---|---|---|---|---|---|---|---|
| $CF_3$ | H | 4-F | 1 | $CF_3$ | F | 4-F | 10 |
| $CF_3$ | H | 4-Cl | 2 | $CF_3$ | F | 4-Cl | 11 |
| $CF_3$ | H | 4-CN | 3 | $CF_3$ | F | 4-CN | 12 |
| $CF_3$ | H | 4-$CF_3$ | 4 | $CF_3$ | F | 4-$CF_3$ | 13 |
| $CF_3$ | H | 4-$CH_3$ | 5 | $CF_3$ | F | 4-$CH_3$ | 14 |
| $CF_3$ | H | 4-$NO_2$ | 6 | $CF_3$ | F | H | 15 |
| $CF_3$—$CF_2$ | H | 4-F | 7 | $CF_3$—$CF_2$ | H | 4-$CF_3$ | 16 |
| $CF_3$—$CF_2$ | H | 4-Cl | 8 | $CF_3$—$CF_2$ | H | 4-$CH_3$ | 17 |
| $CF_3$—$CF_2$ | H | 4-CN | 9 | $CF_3$—$CF_2$ | H | H | 18 |

TABLE 9

| Complex type No | $A_1$ | $A_2$ | $A_3$ | $R_7$ | $R_9$ | X |
|---|---|---|---|---|---|---|
| 7a | COOH | COOH | COOH | $CF_3$ | H | NSC— |
| 7b | COOH | COOH | COOH | $CF_3$ | F | NSC— |
| 7c | COOH | COOH | COOH | $CF_3$ | Cl | NSC— |
| 7d | COOH | COOH | COOH | $CF_3$ | $CH_3$ | NSC— |

TABLE 9-continued

| Complex type No | $A_1$ | $A_2$ | $A_3$ | $R_7$ | $R_9$ | X |
|---|---|---|---|---|---|---|
| 7e | COOH | COOH | $nC_{19}H_{39}$ | $CF_3$ | $CH_3$ | NSC— |
| 7f | COOH | COOH | $nCH(C_{12}H_{25})_2$ | $CF_3$ | $CH_3$ | NSC— |
| 7g | $nC_{19}H_{39}$ | COOH | $nC_{19}H_{39}$ | $CF_3$ | $CH_3$ | NSC— |
| 7h | COOH | $nC_{16}H_{33}$ | $nC_{19}H_{39}$ | $CF_3$ | $CH_3$ | NSC— |
| 7i | COOH | COOH | $NC_{17}H_{35}$ | $CF_3$ | $CH_3$ | NSC— |
| 7j | COOH | COOH | $nCH(C_8H_{17})_2$ | $CF_3$ | $CH_3$ | NSC— |
| 7k | $nC_{17}H_{35}$ | COOH | $nC_{17}H_{35}$ | $CF_3$ | $CH_3$ | NSC— |
| 7l | COOH | $NC_8H_{17}$ | $NC_9H_{19}$ | $CF_3$ | $CH_3$ | NSC— |
| 7m | COOH | COOH | $nC_{19}H_{39}$ | $CF_3$ | F | NSC— |
| 7n | COOH | COOH | $nCH(C_{12}H_{25})_2$ | $CF_3$ | F | NSC— |
| 7o | $nC_{19}H_{39}$ | COOH | $nC_{19}H_{39}$ | $CF_3$ | F | NSC— |
| 7p | COOH | $nC_{16}H_{33}$ | $nC_{19}H_{39}$ | $CF_3$ | F | NSC— |
| 7q | COOH | COOH | $NC_{17}H_{35}$ | $CF_3$ | F | NSC— |
| 7r | COOH | COOH | $nCH(C_8H_{17})_2$ | $CF_3$ | F | NSC— |
| 7s | $nC_{17}H_{35}$ | COOH | $nC_{17}H_{35}$ | $CF_3$ | F | NSC— |
| 7t | COOH | $NC_8H_{17}$ | $NC_9H_{19}$ | $CF_3$ | F | NSC— |
| 7u | COOH | COOH | COOH | $CF_3$ | $CF_3$ | NSC— |

Specifically, preferred illustrative examples of the photosensitizing transition metal complexes of the general formula (Ie) are ruthenium complexes as shown by Complex types 8 to 11 in Table 10 to 13.

TABLE 10

Complex type 8:

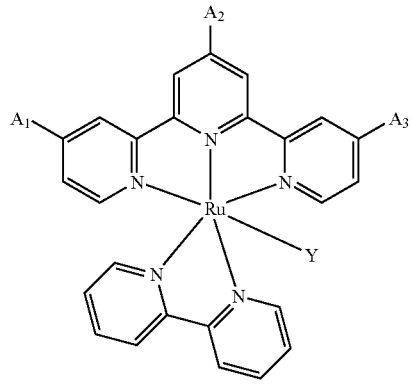

| Complex type No | $A_1$ | $A_2$ | $A_3$ | X |
|---|---|---|---|---|
| 8a | COOH | COOH | $nC_{19}H_{39}$ | NSC— |
| 8b | COOH | COOH | $nCH(C_{12}H_{25})_2$ | NSC— |
| 8c | $nC_{19}H_{39}$ | COOH | $nC_{19}H_{39}$ | NSC— |
| 8d | COOH | $nC_{16}H_{33}$ | $nC_{19}H_{39}$ | NSC— |

TABLE 11

Complex type 9:

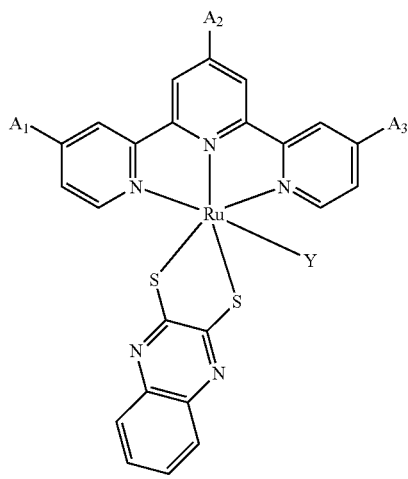

| Complex type No | A$_1$ | A$_2$ | A$_3$ | X |
|---|---|---|---|---|
| 9a | COOH | COOH | nC$_{19}$H$_{39}$ | NSC— |
| 9b | COOH | COOH | nCH(C$_{12}$H$_{25}$)$_2$ | NSC— |
| 9c | nC$_{19}$H$_{39}$ | COOH | nC$_{19}$H$_{39}$ | NSC— |
| 9d | COOH | nC$_{16}$H$_{33}$ | nC$_{19}$H$_{39}$ | NSC— |

TABLE 12

Complex type 10:

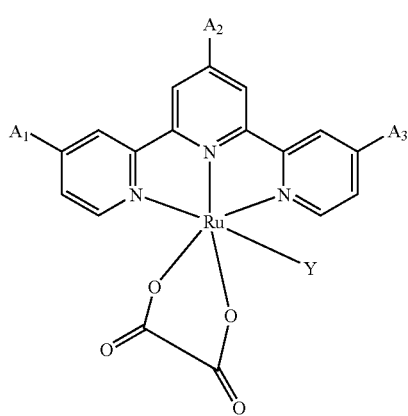

| Complex type No | A1 | A2 | A3 | X |
|---|---|---|---|---|
| 10a | COOH | COOH | nC$_{19}$H$_{39}$ | NSC— |
| 10b | COOH | COOH | nCH(C$_{12}$H$_{25}$)$_2$ | NSC— |
| 10c | nC$_{19}$H$_{39}$ | COOH | nC$_{19}$H$_{39}$ | NSC— |
| 10d | COOH | nC$_{16}$H$_{33}$ | nC$_{19}$H$_{39}$ | NSC— |

TABLE 13

Complex type 11:

| Complex type No | A1 | A2 | A3 | X |
|---|---|---|---|---|
| 11a | COOH | COOH | nC$_{19}$H$_{39}$ | NSC— |
| 11b | COOH | COOH | nCH(C$_{12}$H$_{25}$)$_2$ | NSC— |
| 11c | nC$_{19}$H$_{39}$ | COOH | nC$_{19}$H$_{39}$ | NSC— |
| 11d | COOH | nC$_{16}$H$_{33}$ | nC$_{19}$H$_{39}$ | NSC— |

An embodiment of the present invention will be described with reference to FIG. 1. A dye-sensitized solar cell shown in FIG. 1 has such a structure containing an electroconductive support 8, a porous photovoltaic layer 3 having a photosensitizing dye adsorbed thereon and/or therein formed on the electroconductive support 8, a counter electrode side 9, a hole transporting layer 4 filled between the porous photovoltaic layer 3 and the counter electrode side 9, and a sealant 7 sealing the side surfaces. The electroconductive support 8 is constituted with a substrate 1 and a transparent electroconductive film 2. The material used in the substrate 1 is not particularly limited and can be various kinds of transparent materials, and glass is preferably used. The material used in the transparent electroconductive film 2 is also not particularly limited, and it is preferred to use a transparent electroconductive metallic oxide electrode such as fluorine-doped tin oxide (SnO$_2$:F), antimony doped tin oxide (SnO$_2$:Sb), indium-doped tin oxide (In$_2$O$_3$:Sn), aluminium-doped zinc oxide (ZnO:Al) and gallium-dopped zinc oxide (ZnO:Ga). Examples of the method for forming the transparent electroconductive film 2 on the substrate 1 include a vacuum vapor deposition method, a sputtering method, a CVD (chemical vapor deposition) method and a PVD (physical vapor deposition) method using a component of the material, and a coating method by a sol-gel method.

The material of the porous semiconductor layer used in the porous photovoltaic layer 3 is not particularly limited as far as it is an n-type semiconductor. It is preferred to use an oxide semiconductor such as titanium oxide (TiO$_2$), zinc oxide (ZnO), tin oxide (SnO$_2$), indium oxide (In$_2$O$_3$) and niobium oxide (Nb$_2$O$_3$). It is preferred that the oxide semiconductor have a large surface area for reasons of obtaining high performance of a solar cell. Thus, the oxide semiconductor preferably has a particle diameter of 1 to 200 nm, more preferably 50 nm or less. The oxide semiconductor preferably has a specific surface area of 5 to 100 m2/g. The oxide semiconductor is immobilized on the conductive surface to form a generally porous film having a thickness of at least 200 nm, preferably 1000 to 20000 nm.

A dye sensitized semiconductor electrode according to the present invention may be obtained by fixing the above described metal complex of the present invention to a film or layer of oxide semiconductor particles formed on an electrically conductive surface of a substrate in any suitable conventional manner.

Fixation of the oxide semiconductor on the conductive surface may be effected by dipping or coating in or with a suspension or slurry containing the oxide semiconductor, followed by drying and calcination. A water medium, which may contain a surfactant, a thickening agent such as polyethylene glycol and any suitable additive, is generally used for forming the suspension or slurry. The calcination is generally carried out at 300 to 900° C., preferably 400 to 600° C.

The metal complex is fixed to the semiconductor layer. The metal complex is dissolved in a suitable solvent such as methanol, ethanol, acetonitrile, n-butanol, tert-butanol or dimethylformamide. The above described semiconductor electrode is then impregnated with this solution by immersion, coating or any other suitable method. It is preferred that the solution penetrates deep into the porous layer of the oxide semiconductor. Thus, the semiconductor electrode is preferably evacuated at an elevated temperature to remove gases trapped therein. The metal complex preferably forms a monolayer on surfaces of the oxide semiconductor.

The support on a counter electrode side 9 is constituted by a substrate 5 and a counter electrode layer 6. The material used for the substrate 5 is not particularly limited as similar to the substrate 1, and it can be various kinds of transparent materials, with glass being preferably used. The material used for the counter electrode layer 6 is also not particularly limited, and one of a platinum thin film, a carbon thin film, fluorine-doped tin oxide ($SnO_2$:F), antimony doped tin oxide ($SnO_2$:Sb), tin-doped indium oxide ($In_2O_3$:Sn), aluminium-doped zinc oxide (ZnO:Al) and gallium-dopped zinc oxide (ZnO:Ga), an accumulated layer of plurality thereof, and a composite film of plurality thereof are preferably used. The role of the counter electrode layer 6 is to facilitate the transfer of electrons from the counter electrode to the electrolyte. Examples of the method for forming the counter electrode film 6 on the substrate 5 include a vacuum vapor deposition method, a sputtering method, a CVD (chemical vapor deposition) method and a PVD (physical vapor deposition) method using a component of the material, and a coating method by a sol-gel method. A further possible modification of the counterelectrode is to make it reflective to light that has passed through the electrolyte and the first plate. Further the outside of the substrates may be coated with plastics like PS, PMMA, or preferably PC to protect the TiO2 layer, the dyestuff and the electrolyte against UV-light to give long term stability.

In the present invention, as the hole transporting layer 4 filled between the porous semiconductor layer 3 having the photosensitizing dye adsorbed thereon formed on the electroconductive support 8 and the support on a counter electrode side 9, materials that can transport an electron, a hole or an ion can be used. For example, a hole transporting material such as polyvinyl carbazole, an electron transporting material such as tetranitrofluorenone, an electroconductive polymer such as polypyrrol, a liquid electrolyte, and an ionic electroconductive material such as a polymer solid electrolyte, can be used.

Illustrative of the redox pairs for a liquid electrolyte are I—/$I_3$—, Br—/$Br_3$— and quinone/hydroquinone pairs. In the case of I—/$I_3$—, for example, lithium iodide and iodine may be used. As a solvent for the electrolyte, there may be used an electrochemically inert solvent capable of dissolving the electrolyte in a large amount, such as acetonitrile or propylene carbonate.

The following examples of the present invention will further illustrate.

EXAMPLE 1

Preparation of 4,4',4"-trimethoxycarbonyl-2,2':6',2"-terpyridine

This compound was prepared by an analogous procedure to that described in J. Am. Chem. Soc. 123 (2001) 1613.

EXAMPLE 2

Preparation of 4,4'-diethoxycarbonyl-4"(nonadecyl)-2,2':6',2"-terpyridine, a Compound of the Formula (II2)

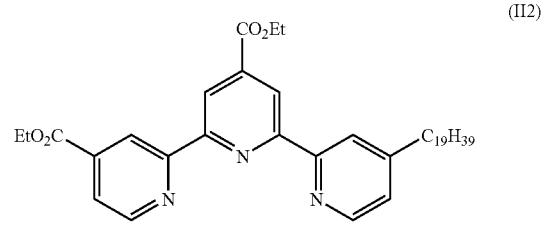

(a) Preparation of 4-nonadecylpyridine (1)

Into a 300-mL flask equipped with a mechanical stirrer, $N_2$ inlet, pressure-equalizing addition funnel which is thermostated in oil bath, were added 14.8 g of sodium amide (0.38 mol) and 64.0 mL of 4-methylpyridine (61.1 g, 0.656 mol). The mixture was stirred under $N_2$ for 1 h while a color change to deep red was observed. A 110-mL sample of n-octadecyl chloride (95.0 g; 0.33 mol) was added to the rapidly stirred reaction mixture over a period of 1.5 h. Shortly after addition was begun, the reaction mixture was warmed to 60° C. to prevent solidification and was subsequently stirred overnight at 100° C. The reaction mixture was cooled to room temperature, diluted with 200 mL of chloroform, washed three times with 200 mL of $H_2O$, and reduced to dryness with the rotary evaporator. The resultant dark brown product was vacuum distilled three times at 0.07 mmHg to finally afford 48.8 g of constant-boiling (180° C. (0.07 mmHg)), white, waxy solid (0.141 mol, 43% yield based on n-octadecyl chloride). Anal. Calcd for $C_{24}H_{43}N$: C, 83.41; H, 12.54; N, 4.05. Found: C, 83.6; H, 12.7; N, 4.0. MS (ESIMS): m/z: 345.3.

(b) Preparation of 2-amino-4-nonadecylpyridine (2)

A mixture of 0.5 molar portion of 4-nonadecylpyridine, 0.59 mole of sodium amide and 1.18 moles of N,N-dimethylaniline was heated at 150° C. for six hours. The reaction mixture, after cooling, was poured into water, and the dimethylaniline layer was separated and dried over anhydrous potassium carbonate. After removal of the solvent in vacuo the residue was stirred in petroleum ether and crystallized from ethyl acetate/ligroin. Yield 45%. Anal. Calcd for $C_{24}H_{44}N_2$: C, 79.93; H, 12.30; N, 7.77. Found: C, 79.63; H, 12.40; N, 7.60. MS (ESIMS): m/z: 360.4.

(c) 2-Bromo-4-nonadecylpyridine (3)

Powdered 2-amino-4-nonadecylpyridine (110.6 g, 0.31 mol) was added under vigorous stirring in portions to 48% hydrobromic acid (500 mL) at 20 to 30° C. in a 4-L glass reactor. After all of the compound was dissolved, the mixture was cooled at −20° C. To this suspension was added cooled bromine (44.3 mL, 0.86 mol) dropwise over 30 min, maintaining the temperature at −20° C. The resulting paste was stirred for 90 min at this temperature. Then sodium nitrite (56.6 g, 0.82 mol) in water (250 mL) was added dropwise. After that the reaction mixture was allowed to warm to 15° C. over 1 h and was stirred for an additional 45 min. The mixture was cooled to −20° C. and treated with cooled aqueous NaOH (222 g, 330 mL $H_2O$). During the addition the temperature was kept at −10° C. maximum. The mixture was allowed to warm to room temperature and stirred for 1 h. The mixture was extracted with ethyl acetate, the organic phase was dried with $Na_2SO_4$, and the solvent was removed in vacuo. The residue was subjected to distillation in vacuo to yield the desired. Yield 50%. Anal. Calcd for $C_{24}H_{42}BrN$: C, 67.90; H, 9.97; N, 3.30. Found: C, 67.50; H, 9.87; N, 3.40. MS (ESIMS): m/z: 423.3.

(d) Preparation of 2-tributyl(4-nonadecylpyridine-2-yl)stannane (4)

To 2-bromo-4-nonadecylpyridine (70.0 g, 165 mmol) in absolute THF (400 mL) at −78° C. was added dropwise n-butyllithium (110 mL, 178 mmol, 1.6 M in hexane). After the solution was stirred at −78° C. for 90 min, tributyltinchloride (53.6 mL, 198 mmol) was added, and the mixture was allowed to warm to room temperature. Water (90 mL) was poured into the reaction mixture, and the phases were separated. The aqueous layer was extracted with diethyl ether (4×200 mL). The combined organic phases were dried over $Na_2SO_4$, and the solvent was removed in vacuo. The resulting oil was purified by fractionated Kugelrohr distillation. Selected analytical data follows. Yield: 55%. Anal. $C_{36}H_{69}NSn$: Calcd: C, 68.13; H, 10.96; N, 2.21. Found: C, 68.65; H, 10.76; N, 2.27. MS (ESIMS): m/z: 635.4.

(e) Preparation of 2-tributylstannyl-picolines (5)

To 2-bromo-picoline (28.4 g, 165 mmol) in absolute THF (250 mL) at −78° C. was added dropwise n-butyllithium (110 mL, 178 mmol, 1.6 M in hexane). After the solution was stirred at −78° C. for 90 min, tributyltinchloride (53.6 mL, 198 mmol) was added, and the mixture was allowed to warm to room temperature. Water (90 mL) was poured into the reaction mixture, and the phases were separated. The aqueous layer was extracted with diethyl ether (4×200 mL). The combined organic phases were dried over $Na_2SO_4$, and the solvent was removed in vacuo. The resulting oil was purified by fractionated Kugelrohr distillation. Colorless liquid, bp 120° C. (2.5×10$^{-5}$ mbar), Yield 60%; Anal. $C_{18}H_{33}NSn$: Calcd: C, 56.56; H, 8.64; N, 3.67. Found: C, 56.22; H, 8.70; N, 3.21. MS (ESIMS): m/z: 383.2.

(f) Preparation of 2,6-dihydroxy-4-methylpyridine (6)

A mixture of 2,6-dihydroxy-3-cyano-4-methylpyridine (4.32 g, 28.8 mmol), concentrated $H_2SO_4$ (12 mL) and water (10 mL) was heated under reflux for 5 h. The mixture was cooled with ice and neutralized with solid $NaHCO_3$. The precipitate was filtered, washed with water and $Et_2O$ and dried in vacuo to give a mixture of 2,6-dihydroxy-4-methylpyridine and of the free acid, which was not decarboxylated. The mixture was used without further purification for the next reaction step. Yield: 72%. Anal. $C_6H_7NO_2$: Calcd: C, 57.59; H, 5.64; N, 11.19; O, 25.57. Found: C, 57.74; H, 5.55; N, 11.19; O, 25.66. MS (ESIMS): m/z: 125.0.

(g) Preparation of 2,6-dibromo-4-methylpyridine (7)

Compound 6 (1.0 g, 7.93 mmol) and $POBr_3$ (7.26 g, 25.33 mmol) were ground and melted together at 140-150 C for 1 h. After cooling, the mixture was quenched with water, neutralized with solid $NaHCO_3$ and extracted with $CHCl_3$ (3×100 mL). The combined organic phases were washed with water and purified by column chromatography on silica with hexane/EOAc (9/1, v/v) to give 2,6-dibromo-4-methylpyridine as a colorless oil. Yield: 58%. Anal. $C_6H_5Br_2N$: Calcd: C, 28.72; H, 2.01; N, 5.58. Found: C, 28.58; H, 2.07; N, 5.46. MS (ESIMS): m/z: 250.9.

(h) Preparation of 6-bromo-4,4'-dimethyl-2,2'-bipyridine (8)

Dibromocompound 2,6-dibromo-4-methylpyridine (1 mmol), 2-tributylstannyl-picolines (1 mol) and $(Ph_3Ph)_4Pd$ (0.01 equiv) were heated under $N_2$ in toluene (50 mL) for 16 h. Upon cooling to room temperature aqueous saturated $NH_4Cl$ solution (20 mL) was added. The mixture was stirred for further 30 min and then filtered over Celite. The precipitate was washed with $CH_2Cl_2$ (50 mL) and the organic phase was separated. The aqueous phase was extracted with toluene. The combined organic phases were dried ($MgSO_4$) and the solvent was removed. Concentrated HCl (30 mL) was added to the residue followed by extracting with $CH_2Cl_2$. The aqueous phase was cautiously neutralized by solid NaOH. The product was then extracted with $CH_2Cl_2$ and dried. The solvent was removed and the product purified by chromatography on silica gel with $CH_2Cl_2$/hexane (1:2) as eluent. Yield: 25%. Anal. $C_{12}H_{11}BrN_2$: Calcd: C, 54.77; H, 4.21; N, 10.65. Found: C, 54.54; H, 4.30; N, 10.45. MS (ESIMS): m/z: 262.0.

(i) Preparation of 6-bromo-4,4'-dicarboxy-2,2'-bipyridine (9)

To a stirring solution of sulfuric acid (98%, 125 mL), 5.37 g (20.5 mmoles) of 6-bromo-4,4'-dimethyl-2,2'-bipyridine was added. With efficient stirring, 24 g (81.5 mmoles) of potassium dichromate was then added in small portions, such that the temperature remained between 70 and 80° C. Occasional cooling in a water bath was usually necessary during the addition of potassium dichromate. After all the potassium dichromate was added, the reaction stirred at room temperature until the temperature fell below 40° C. The deep green reaction mixture was poured into 800 mL of ice water and filtered. The solid was washed with water until the filtrate was colorless and allowed to dry. The resulting light yellow solid was then further purified by refluxing it in 170 mL of 50% nitric acid for 4 hours. This solution was poured over ice, diluted with 1 L of water and cooled to 5° C. The precipitate was filtered, washed with water (5×50 mL), then acetone (2×20 mL) and allowed to dry giving 6.2 g (94%) of 6-bromo-4,4'-dicarboxy-2,2'-bipyridine as a fine white solid. Anal. $C_{12}H_7BrN_2O_4$: Calcd: C, 44.61; H, 2.18; N, 8.67. Found: C, 44.23; H, 2.14; N, 8.56. MS (ESIMS): m/z: 322.0.

(j) Preparation of 6-bromo-4,4'-diethoxycarbonyl-2,2'-bipyridine (10)

To a suspension of 6-bromo-4,4'-dicarboxy-2,2'bipyridine (6.6 g, 20.5 mmol) in 400 mL of absolute ethanol was added 5 mL of concentrated sulfuric acid. The mixture was refluxed for 80 h to obtain a clear solution and then cooled to room temperature. Water (400 mL) was added and the excess ethanol removed under vacuum. The pH was adjusted to neutral with NaOH solution, and the resulting precipitate was filtered and washed with water (pH=7). The solid was dried to obtain 7.0 g (90%) of 6-bromo-4,4'-diethoxycarbonyl-2,2'-bipyridine. Anal. $C_{16}H_{15}BrN_2O_4$: Calcd C, 50.68; H, 3.99; N, 7.39. Found: C, 50.45; H, 3.92; N, 7.33. MS (ESIMS): m/z: 378.0.

(k) Preparation of 4,4'-diethoxycarbonyl-4"(nonadecyl)-2,2':6',2"-terpyridine (11)

6-Bromo-4,4'-diethoxycarbonyl-2,2'-bipyridine (10) (1 mmol), 2-tributyl(4-nonadecylpyridine-2-yl)stannane (4) (1 mmol) and $(Ph_3P)4Pd$ (0.01 equiv) were heated under $N_2$ in toluene (50 mL) for 16 h. Upon cooling to room temperature aqueous saturated NH4Cl solution (20 mL) was added. The mixture was stirred for further 30 min and then filtered over celite. The precipitate was washed with $CH_2Cl_2$ (50 mL) and the organic phase was separated. The aqueous phase was extracted with toluene. The combined organic phase were dried ($MgSO_4$) and the solvent was removed. Concentrated HCl (30 mL) was added to the residue and extracted with $CH_2Cl_2$. The aqueous phase was cautiously neutralized by solid NaOH. The product was then extracted with $CH_2Cl_2$ and dried. The solvent was removed and the product purified by chromatography on silica gel with $CH_2Cl_2$/hexane (1:2) as eluent. Yield: 25%. Anal. $C_{40}H_{57}N_3O_4$ Calcd: C, 74.61; H, 8.92; N, 6.53. Found: C, 74.22; H, 8.72; N, 6.49. MS (ESIMS): m/z: 643.4.

EXAMPLE 3

Preparation of 4,4'-diethoxycarbonyl-4"-(didodecylmethyl)-2,2':6',2"-terpyridine, a Compound of the Formula (II3)

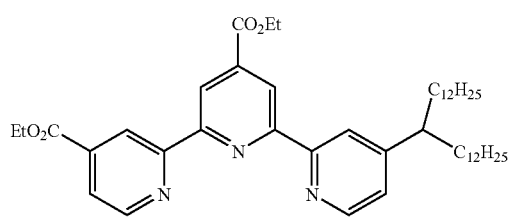
(II3)

(a) Preparation of 4-(didodecylmethyl)pyridine (1)

A solution of butyllithium (1.6 M in hexane; 2.05 equiv.) was added to a solution of diisopropylamine (0.2 M; 2.1 equiv.) in dry ether at −15° C. After stirring for 30 min, freshly distilled 4-methylpyridine (1 eqiv.) was added dropwise. The resulting red solution was stirred for 15 min at −15° C. and then a solution of alkyl halide (1 M; 2.05 equiv.) in dry ether was added in one portion. The mixture was stirred overnight at room temperature. Ether was added and the reaction mixture was washed twice with 1 M $NH_4Cl$ solution, dried with $Na_2SO_4$ and evaporated to dryness. The product was purified by chromatography on $Al_2O_3$ (neutral), gradient-eluting with hexane and finally hexane/ether (5:1) to give the product in yield 70%. Anal. $C_{30}H_{55}N$: Calcd: C, 83.84; H, 12.90; N, 3.26. Found: C, 83.55; H, 12.84; N, 3.21. MS (ESIMS): m/z: 429.4.

(b) Preparation of 2-amino-4-didodecylmethyl-pyridine (2)

This compound was prepared by an analogous procedure to that descrived in Example 2 (step b). Anal. $C_{30}H_{56}N_2$: Calcd: C, 81.01; H, 12.69; N, 6.30. Found: C, 81.11; H, 12.77; N, 6.25. MS (ESIMS): m/z: 444.8.

(c) Preparation of 2-Bromo-4-didodecylmethyl-pyridine (3)

This compound was prepared by an analogous procedure to that descrived in Example 2 (step c). Anal. $C_{30}H_{54}BrN$: Calcd: C, 70.84; H, 10.70; N, 2.75. Found: C, 70.45; H, 10.67; N, 2.69. MS (ESIMS): m/z: 507.3.

(d) Preparation of 2-tributyl(4-didodecylmethyl-2-yl)stannane (4)

This compound was prepared by an analogous procedure to that described in Example 2 (step d). Anal. $C_{42}H_{81}NSn$: Calcd: C, 70.18; H, 11.36; N, 1.95. Found: C, 70.0; H, 11.31; N, 1.97. MS (ESIMS): m/z: 719.5.

(e) Preparation of 6-bromo-4,4'-diethoxycarbonyl-2, 2'-bipyridine (5)

This compound was prepared by an analogous procedure to that described in Example 2 (step e-j). Anal. $C_{16}H_{15}BrN_2O_4$: Calcd C, 50.68; H, 3.99; N, 7.39. Found: C, 50.35; H, 3.78; N, 7.34. MS (ESIMS): m/z: 379.02.

(f) Preparation of 4,4'-diethoxycarbonyl-4"-didodecylmethyl-2,2':6',2"-terpyridine (6)

This compound was prepared by an analogous procedure to that described in Example 2 (step k). Anal. $C_{46}H_{69}N_3O_4$: Calcd: C, 75.89; H, 9.55; N, 5.77; O, 8.79. Found: C, 75.89; H, 9.55; N, 5.77; O, 8.79. MS (ESIMS): m/z: 728.0.

EXAMPLE 4

Preparation of 4,4'-bis(diethylphosphonato)-4"-nonadecyl-2,2':6',2"-terpyridine, a Compound of the Formula (II4)

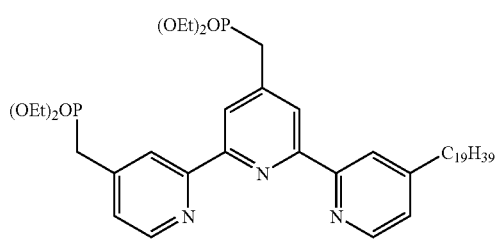
(II4)

(a) Preparation of 4,4'-diethoxycarbonyl-4"-nonadecyl-2,2':6',2"-terpyridine

This compound was prepared by an analogous procedure to that described in Example 2.

(b) Preparation of 4,4'-bis(hydroxymethyl)-4"-nonadecyl-2,2':6',2"-terpyridine 8.2 g of sodium borohydride was added to a suspension of 4,4'-diethoxycarbonyl-4"-nonadecyl-2,2':6',2"-terpyridine (6.4 g, 10.0 mmol) in 200 mL of absolute ethanol. The mixture was refluxed for 3 h and cooled to room temperature, and then 200 mL of an ammonium chloride saturated water solution was added to decompose the excess borohydride. The ethanol was removed under vacuum and the precipitated solid was dissolved in a minimal amount of water. The resulting solution was extracted with ethyl acetate (5×200 mL) and dried over sodium sulfate, and the solvent was removed under vacuum. The desired solid was obtained in 79% yield and was used without further purification. Anal. $C_{36}H_{53}N_3O_2$: Calcd: C, 77.24; H, 9.54; N, 7.51. Found: C, 77.10; H, 9.47; N, 7.49. MS (ESIMS): m/z: 559.4.

(c) Preparation of 4,4'-bis(bromomethyl)-4"-nonadecyl-2,2':6',2"-terpyridine 4,4'-Bis(hydroxymethyl)-4"-nonadecyl-2,2':6',2"-terpyridine (2.35 g, 4.2 mmol) was dissolved in a mixture of 48% HBr (20 mL) and concentrated sulfuric acid (6.7 mL). The resulting solution was refluxed for 6 h and then allowed to cool to room temperature, and 40 mL of water was added. The pH was adjusted to neutral with NaOH solution and the resulting precipitate was filtered, washed with water (pH) 7), and air-dried. The product was dissolved in chloroform (40 mL) and filtered. The solution was dried over magnesium sulfate and evaporated to dryness, yielding 2.45 g of 4,4'-bis(bromomethyl)-4"-nonadecyl-2,2':6',2"-terpyridine (85% yield) as a white powder. Anal. $C_{36}H_{51}Br_2N_3$: calcd C, 63.07; H, 7.50; N, 6.13; found C, 62.88; H, 7.45; N, 6.19. MS (ESIMS): m/z: 685.2.

(d) Preparation of 4,4'-bis(diethylmethylphosphonate)-4"-nonadecyl-2,2':6',2"-terpyridine A chloroform (10 mL) solution of 4,4'-Bis(bromomethyl)-4"-nonadecyl-2,2':6',2"-terpyridine (3.02 g, 4.4 mmol) and 15 mL of triethyl phosphite was refluxed for 3 h under nitrogen. The excess phosphite was removed under high vacuum, and then the crude product was purified by column chromatography on silica gel (eluent ethyl acetate/methanol 80/20) yielding 2.82 g (80%) of 4,4'-bis(diethylmethylphosphonate)-4"-nonadecyl-2,2':6',2"-terpyridine. Anal. $C_{44}H_{71}N_3O_6P_2$: calcd C, 66.06; H, 8.95; N, 5.25; found C, 65.67; H, 8.88; N, 5.45. MS (ESIMS): m/z: 799.5.

EXAMPLE 5

Preparation of 4'-ethoxycarbonyl-4,4"-bis(nonadecyl)-2,2':6',2"-terpyridine, a Compound of the Formula (II5)

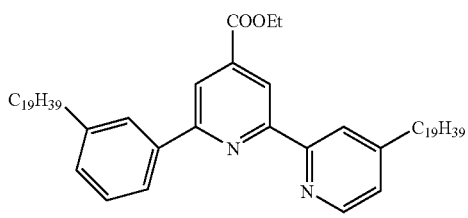

(II5)

(a) Preparation of 2,6-dibromo-4-carboxy-pyridine (1)

This compound was prepared by an analogous procedure to that described in Example 2 (step g). Anal. $C_6H_3Br_2NO_2$: Calcd: C, 25.65; H, 1.08; Br, 56.89; N, 4.99; O, 11.39. Found: C, 25.52; H, 1.14; Br, 56.77; N, 5.04; O, 11.25. (ESIMS): m/z: 280.9.

(b) Preparation of 2,6-dibromo-4-ethoxycarbonyl-pyridine (2)

This compound was prepared by an analogous procedure to that described in Example 2 (step j). Anal. $C_8H_7Br_2NO_2$: Calcd: C, 31.10; H, 2.28; Br, 51.73; N, 4.53; O, 10.36. Found: C, 31.22; H, 2.15; Br, 51.81; N, 4.45; O, 10.31. (ESIMS): m/z: 308.9.

(c) Preparation of 2-tributyl(4-nonadecylpyridine-2-yl)stannane (3)

This compound was prepared by an analogous procedure to that described in Example 2 (step d).

(d) Preparation of 4'-ethoxycarbonyl-4,4"-bis(nonadecyl_)-2,2':6',2"-terpyridine (4)

2,6-Dibromo-4-ethoxycarbonyl-pyridine(2) (1 mol), 2-tributyl(4-nonadecylpyridine-2-yl)stannane (2 mol) and $(Ph_3P)_4Pd$ (0.01 equiv) were heated under $N_2$ in toluene (50 mL) for 16 h. Upon cooling to room temperature aqueous saturated $NH_4Cl$ solution (20 mL) was added. The mixture was stirred for further 30 min and then filtered over Celite. The precipitate was washed with $CH_2Cl_2$ (50 mL) and the organic phase was separated. The aqueous phases was extracted with toluene. The combined organic phases were dried ($MgSO_4$) and the solvent was removed. Concentrated HCl (30 mL) was added to the residue, followed by extracting with $CH_2Cl_2$. The aqueous phase was cautiously neutralized by solid NaOH. The product was then extracted with $CH_2Cl_2$ and dried. The solvent was removed and the product was purified by chromatography on silica gel with $CH_2Cl_2$/hexane (1:2) as eluent. Yield: (25%). Anal. $C_{56}H_{91}N_3O_2$: Calcd: C, 80.23; H, 10.94; N, 5.01; O, 3.82. Found: C, 80.05; 10.99; N, 5.23; O, 3.71, MS (ESIMS): m/z: 837.7.

EXAMPLE 6

Preparation of 4-nonadecyl-4'-hexadecyl-4"-ethoxycarbonyl-2,2':6',2"-terpyridine, a Compound of the Formula (II6)

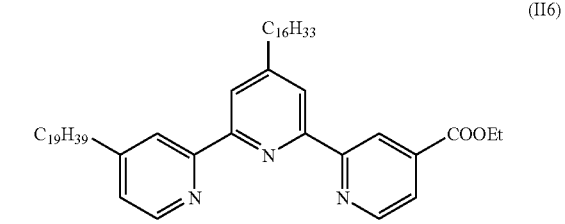

(II6)

(a) Preparation of 3-oxo-nonadecanoic Acid Ethyl Ester (1)

To a solution of sodium hydride (1.2 g, 50 mmol) in THF, distilled ethyl acetoacetate (4.16 g, 32 mmol) was added dropwise. The resulting mixture was stirred for 30 min at room temperature and then cooled at −78° C. A solution of n-butyllithium in hexane (16.1 mL, 35.2 mmol) was added dropwise. After stirring for an additional 1 h at 0° C., 1-bromohexadecane (19.1 mmol) in THF was added and the mixture was stirred for 12 h. Ethanol (15 mL) was added slowly at room temperature. The resulting solution was filtered through a Celite pad, concentrated in vaccum and purified by chromatography on silica gel to give the 3-oxo-nonadecanoic acid ethyl ester as a solid. Anal. $C_{21}H_{40}O_3$: Calcd: C, 74.07; H, 11.84; O, 14.09. Found: C, 73.98; H, 11.59; O, 14.25. MS (ESIMS): m/z: 340.3.

(b) Preparation of 3-cyano-2,6-dihydroxy-4-hexadecyl-pyridine (2)

3-Oxo-nonadecanoic acid ethyl ester (11.3 mmol), cyanoacetamide (0.95 g, 11.3 mmol) and piperidine (0.95 g, 11.3 mmol) in MeOH (3 mL) were heated under reflux for 24 h. The solvent was evaporated, and the residue was dissolved in hot water. The product was precipitated by addition of concentrated HCl, filtered, washed with ice water and $CHCl_3$ and dried in vaccum to give 3-cyano-2,6-dihydroxy-4-hexadecyl-pyridine as a white powder. Yield: 40%. Anal. $C_{22}H_{36}N_2O_2$: Calcd: C, 73.29; H, 10.06; N, 7.77; O, 8.88. Found: C, 73.35; H, 10.12; N, 7.85; O, 8.97. MS (ESIMS): m/z: 360.3.

(c) Preparation of 2,6-dihydroxy-4-hexadecyl-pyridine (3)

This compound was prepared by an analogous procedure to that described in Example 2 (step f). Anal. C21H37NO2: Calcd: C, 75.17; H, 11.12; N, 4.17; O, 9.54. Found: C, 75.03; H, 11.09; N, 4.25; O, 9.38. MS (ESIMS): m/z: 335.3.

(d) Preparation of 2,6-dibromo-4-hexadecyl-pyridine (4)

This compound was prepared by an analogous procedure to that described in Example 2 (step g). Anal. $C_{21}H_{35}Br_2N$: Calcd: C, 54.67; H, 7.65; Br, 34.64; N, 3.04. Found: C, 54.84; H, 7.61; Br, 34.52; N, 3.11. MS (ESIMS): m/z: 461.1.

(e) Preparation of 2-tributyl(4-nonadecylpyridine-2-yl)stannane (5)

This compound was prepared by an analogous procedure to that described in Example 2 (steps a-d).

(f) Preparation of 6-Bromo-4-hexadecyl-4'-nonadecyl-2,2'-bipyridine (6)

This compound was prepared by an analogous procedure to that described in Example 2 (step h). Anal. $C_{45}H_{77}BrN_2$: Calcd: C, 74.45; H, 10.69; Br, 11.01; N, 3.86. Found: C, 74.59; H, 10.84; Br, 11.13; N, 3.82. MS (ESIMS): m/z: 724.5.

(g) Preparation of 6-tributylstannyl-4-hexadecyl-4'-nonadecyl-2,2'-bipyridine (7)

This compound was prepared by an analogous procedure to that described in Example 2 (step e). Anal. $C_{57}H_{104}N_2Sn$: Calcd: C, 73.13; H, 11.20; N, 2.99; Sn, 12.68. Found: C, 73.22; H, 11.28; N, 3.01; Sn, 12.59. MS (ESIMS): m/z: 936.7.

(h) Preparation of 2-bromo-4-carboxy-pyridine (8)

This compound was prepared by an analogous procedure to that described in Example 2 (step i). Anal. $C_6H_4BrNO_2$: Calcd: C, 35.67; H, 2.00; Br, 39.56; N, 6.93; O, 15.84. Found: C, 35.75; H, 2.03; Br, 39.61; N, 6.90; O, 15.77. MS (ESIMS): m/z: 200.9.

(i) Preparation of 2-bromo-4-ethoxycarbonyl-pyridine (9)

This compound was prepared by an analogous procedure to that described in Example 2 (step j). Anal. $C_8H_8BrNO_2$: Calcd: C, 41.77; H, 3.50; Br, 34.73; N, 6.09; O, 13.91. Found: C, 41.87; H, 3.45; Br, 34.82; N, 6.03; O, 14.01. MS (ESIMS): m/z: 229.0.

(j) Preparation of 4-(nonadecyl)-4'-(hexadecyl)-4"(ethoxycarbonyl)-2,2':6',2"-terpyridine (10)

This compound was prepared by an analogous procedure to that described in Example 2 (step k). Anal. $C_{53}H_{85}N_3O_2$: Calcd: C, 79.94; H, 10.76; N, 5.28; O, 4.02. Found: C, 79.89; H, 10.70; N, 5.31; O, 3.98. MS (ESIMS): m/z: 795.7.

EXAMPLE 7

Preparation of 2,6-bis-(aminomethyl)-pyridine (formula IIIc)

(a) Preparation of 2,6-bis-(bromomethyl)-pyridine (Synthesis ref. J. Am. Chem. Soc. 1977, 99, 6392.)

(b) 2,6-bis-(aminomethyl)-pyridine

To a solution of hexamethylenetriamine (10.4 mmol) in $CHCl_3$ (50 mL) heated at reflux, a solution of 2,6-bis-(bromomethyl)-pyridine (4.97 mmol) in $CHCl_3$ (50 mL) was added dropwise, and the mixture was refluxed for further 3 h. The mixture was allowed to cool to room temperature and to stand. The solid deposited was filtered off, dried, and suspended in $H_2O$/EtOH/conc. HCl. The mixture was stirred at 70° C. until the solid had completely dissolved. The salt (2,6-bis-(aminomethyl)-pyridine). HCl which was crystallized from solution on standing overnight at room temperature was filtered off and dried. Yield 70%. Anal. $C_7H_{11}N_3$: Calcd: C, 61.29; H, 8.08; N, 30.63. Found: C, 61.45; H, 8.00; N, 30.44. MS (ESIMS): m/z: 137.1.

EXAMPLE 8

Preparation of 2-hydroxy-1,3-benzenedicarboxylic Acid (Formula IIId)

This compound was prepared from 2-methoxyisophthalic acid by an analogous procedure to that described in reference Chem. Bar 1889, 12, 816. Anal. $C_8H_6O_5$: Calcd: C, 52.76; H, 3.32; O, 43.92. Found: C, 52.45; H, 3.30; O, 43.52. MS (ESIMS): m/z: 182.0.

EXAMPLE 9

Complex 1a

Preparation of the complex of the formula $RuLY^1$, wherein L is 4,4'4"-tricarboxy-2,2':6',2"-terpyridine and $Y^1$ is diethylenetriamine(deta).

(a) Preparation of Ru(4,4'4"-trimethoxycarbonyl-2,2':6',2"-terpyridine)Cl$_3$

Ethyl alcohol (50 ml) and RuCl$_3$ (0.26 g) were reacted under argon. After the mixture was stirred for 2 min, a solution of the ligand 4,4'4"-Trimethoxycarbonyl-2,2':6',2"-terpyridine, 0.4 g, in 50 mL of dichloromethane, was then added. The reaction mixture was refluxed for 2 h under argon. The solution was concentrated to 20 mL, and the reaction mixture was cooled to room temperature. The precipitated complex, Ru(4,4'4"-Trimethoxycarbonyl-2,2':6',2"-terpyridine)Cl$_3$, was collected on a sintered glass crucible and was washed with ethanol. (yield 85%) Anal. $C_{21}H_{17}Cl_3N_3O_6Ru$: Calcd: C, 41.03; H, 2.79; N, 6.83. Found: C, 41.30; H, 2.67; N, 6.76. MS (ESIMS): m/z: 613.9.

(b) Preparation of Ru(4,4'4"-tricarboxy-2,2':6',2"-terpyridine)(deta)

To a solution of the complex Ru(4,4'4"-trimethoxycarbonyl-2,2':6',2"-terpyridine)Cl$_3$ (300 mg, 0.5 mmol) in DMF (100 mL) was added diethylenetriamine (2.0 mmol) and Et$_3$N (0.5 mL). The reaction mixture was refluxed for 8 h. Then, 10 mL of Et$_3$N was added, and the solution was refluxed for further 24 h to hydrolyze the ester groups on the terpyridine ligand. The reaction mixture was allowed to cool, and the solvent was removed on a rotary evaporator. The resulting solid was dissolved in 0.1 M aqueous NaOH and Ru(4,4'4"-tricarboxy-2,2':6',2"-terpyridine)(deta) was precipitated by the addition of 0.1 M HNO$_3$. The resulting precipitate was filtered and dried. The isolated solid was recrystallized from methanol-diethyl ether, after which it was further purified on a Sephadex LH$_2$O column, using methanol as eluent (yield 75%). Anal. $C_{22}H_{24}Cl_2N_6O_6Ru$: Calcd: C, 41.26; H, 3.78; N, 13.12. Found: C, 41.04; H, 3.73; N, 13.03. MS (ESIMS): m/z: 640.02.

EXAMPLE 10

Complex 2a

Preparation of the complex of the formula $RuLY^1(TBA)_2$, wherein L is 4,4'4"-tricarboxy-2,2':6',2"-terpyridine, $Y^1$ is 2,6-pyridinedimethanol(pdm) and TBA is tetrabutylammonium ion.

(a) Preparation of Ru(4,4'4"-trimethoxycarbonyl-2,2':6',2"-terpyridine)Cl$_3$

This compound was prepared by an analogous procedure to that described in Example 9 (step a).

(b) Preparation of Ru(4,4'4"-tricarboxy-2,2':6',2"-terpyridine)(pdm)

This compound was prepared by an analogous procedure to that described in Example 9 (step b). Anal. $C_{25}H_{18}N_4O_8Ru$: Calcd C, 49.75; H, 3.01; N, 9.28. Found: C, 49.75; H, 3.01; N, 9.28. MS (ESIMS): m/z: 604.02.

(c) Preparation of Ru(4,4'4"-tricarboxy-2,2':6',2"-terpyridine)(pdm)(TBA)$_2$

Powder Ru(4,4'4"-tricarboxy-2,2':6',2"-terpyridine)(pdm) was dissolved in 0.1 M aqueous tetrabutylammonium hydroxide (TBAOH) and the mixture heated to 110° C., for 4 h (the pH of the solution was about 11). The resulting purple solution was filtered to remove a small amount of insoluble material and the pH was adjusted to 5.0 with dilute hydrochloric acid. A dense precipitate formed immediately but the suspension was nevertheless refrigerated overnight prior to filtration to collect the product. After allowing to cool to (25° C.) room temperature, it was filtered through a sintered glass crucible and dried under vacuum. Anal. $C_{57}H_{88}N_6O_8Ru$: Calcd: C, 63.02; H, 8.16; N, 7.7. Found: C, 63.02; H, 8.16; N, 7.7. MS (ESIMS): m/z: 1086.57.

EXAMPLE 11

Complex 1b

Preparation of the complex of the formula $RuLY^1$, wherein L is 4,4'-dicarboxy-4"-nonadecyl-2,2':6',2"-terpyridine and $Y^1$ is diethylenetriamine(deta).

(a) Preparation of Ru(4,4'-diethoxycarbonyl-4"-nonadecyl-2,2':6',2"-terpyridine)Cl$_3$ This compound was prepared by an analogous procedure to that described in Example 9 (step a). Anal. $C_{39}H_{53}Cl_3N_3O_6Ru$: Calcd: C, 54.01; H, 6.16; N, 4.85. Found: C, 53.80; H, 6.13; N, 4.77. MS (ESIMS): m/z: 866.20.

(b) Preparation of Ru(4,4'-dicarboxy-4"-nonadecyl-2,2':6',2"-terpyridine)(deta)

This compound was prepared by an analogous procedure to that described in Example 9 (step b). Anal. $C_{41}H_{62}N_6O_6Ru$: Calcd C, 58.90; H, 7.47; N, 10.05. Found: C, 58.90; H, 7.47; N, 10.05. MS (ESIMS): m/z: 836.38.

EXAMPLE 12

Complex 2b

Preparation of the complex of the formula $RuLY^1(TBA)$, wherein L is 4,4'-dicarboxy-4"-nonadecyl-2,2':6',2"-terpyridine and $Y^1$ is 2,6-pyridinedimethanol (pdm) and TBA is tetrabutylammonium ion.

(a) Preparation of Ru(4,4'-diethoxycarbonyl-4"-nonadecyl-2,2':6',2"-terpyridine)Cl$_3$ This compound was prepared by an analogous procedure to that described in Example 9 (step a).

(b) Preparation of Ru(4,4'-dicarboxy-4"-nonadecyl-2,2':6',2"-terpyridine)(pdm)

This compound was prepared by an analogous procedure to that described in Example 9 (step b). Anal. $C_{44}H_{56}N_4O_8Ru$: Calcd C, 58.90; H, 7.47; N, 10.05. Found: C, 58.90; H, 7.47; N, 10.05. MS (ESIMS): m/z: 870.31.

(c) Preparation of Ru(4,4'-dicarboxy-4"-nonadecyl-2, 2':6',2"-terpyridine)(pdm)(TBA)

This compound was prepared by an analogous procedure to that described in Example 10 (step c). Anal. $C_{60}H_{91}N_5O_8Ru$: Calcd C, 64.84; H, 8.25; N, 6.30. Found: C, 64.84; H, 8.25; N, 6.30. MS (ESIMS): m/z: 1111.59.

EXAMPLE 13

Complex 3a

Preparation of the Complex of the Formula RuLY$^1$, Wherein L is 4,4'4"-tricarboxy-2,2':6',2"-terpyridine and Y$^1$ is 2,6-bis-(aminomethyl)-pyridine(bamp).

(a) Preparation of Ru(4,4'4"-trimethoxycarbonyl-2, 2':6',2"-terpyridine)Cl$_3$

This compound was prepared by an analogous procedure to that described in Example 9 (step a).

(b) Preparation of Ru(4,4'4"-tricarboxy-2,2':6',2"-terpyridine)(bamp)

This compound was prepared by an analogous procedure to that described in Example 9 (step b). Anal. $C_{25}H_{22}N_6O_6Ru$: Calcd C, 49.75; H, 3.67; N, 13.92. Found: C, 49.23; H, 3.61; N, 13.88. MS (ESIMS): m/z: 604.06.

EXAMPLE 14

Complex 3c

Preparation of the complex of the formula RuLY$^1$, wherein L$^1$ is 4,4'-Dicarboxy-4"-nonadecyl-2,2':6',2"-terpyridine and Y$^1$ is 2,6-Bis-(aminomethyl)-pyridine (bamp).

(a) Preparation of Ru(4,4'-diethoxycarbonyl-4"-nonadecyl-2,2':6',2"-terpyridine)Cl$_3$ This compound was prepared by an analogous procedure to that described in Example 9 (step a).

(b) Preparation of Ru(4,4'-dicarboxy-4"-nonadecyl-2,2':6',2"-terpyridine)(bamp)

This compound was prepared by an analogous procedure to that described in Example 9 (step b). Anal. $C_{44}H_{60}N_6O_6Ru$: Calcd C, 60.74; H, 6.95; N, 9.66. Found: C, 60.74; H, 6.95; N, 9.66. MS (ESIMS): m/z: 870.36.

EXAMPLE 15

Complex 4a

Preparation of the complex of the formula RuLY$^1$ (TBA)$_3$, wherein L is 4,4'4"-tricarboxy-2,2':6',2"-terpyridine, Y$^1$ is 2-hydroxy-1,3-benzenedicarboxilic acid(hbdc) and TBA is tetrabutylammonium ion.

(a) Preparation of Ru(4,4'4"-trimethoxycarbonyl-2, 2':6',2"-terpyridine)Cl$_3$

This compound was prepared by an analogous procedure to that described in Example 9 (step a).

(b) Preparation of Ru(4,4'4"-tricarboxy-2,2':6',2"-terpyridine)(hbdc)

This compound was prepared by an analogous procedure to that described in Example 9 (step b). Anal. $C_{26}H_{14}N_3O_{11}Ru$: Calcd C, 48.38; H, 2.19; N, 6.51. Found: C, 48.05; H, 2.11; N, 6.61. MS (ESIMS): m/z: 645.97.

(c) Preparation of Ru(4,4'4"-tricarboxy-2,2':6',2"-terpyridine)(hbdc)(TBA)$_3$

This compound was prepared by an analogous procedure to that described in Example 10 (step c). Anal. $C_{75}H_{124}N_6O_{11}Ru$: Calcd: C, 64.95; H, 9.01; N, 6.06. Found: C, 64.34; H, 9.12; N, 6.00. MS (ESIMS): m/z: 1386.84.

EXAMPLE 16

Complex 5a

Preparation of the complex of the formula RuL(NCS)$_3$ (TBA)$_2$, wherein L is 4,4'-dicarboxy-4"-nonadecyl-2,2':6', 2"-terpyridine (formula 2) and TBA is tetrabutylammonium ion.

(a) Preparation of Ru(4,4'-diethoxycarbonyl-4"-nonadecyl-2,2':6',2"-terpyridine)Cl$_3$ This compound was prepared by an analogous procedure to that described in Example 9 (step a). Anal. $C_{40}H_{67}Cl_3N_3O_4Ru$: Calcd: C, 56.43; H, 6.75; N, 4.94. Found: C, 56.12; H, 6.65; N, 4.87. MS (ESIMS): m/z: 850.25.

(b) Preparation of Ru(4,4'-dicarboxy-4"-nonadecyl-2,2':6',2"-terpyridine)(NCS)$_3$ The complex Ru(4,4'-diethoxycarbonyl-4"-nonadecyl-2, 2':6',2"-terpyridine)(NCS)$_3$ was synthesized in dark under an argon atmosphere by refluxing at 130° C., a solution of NH$_4$NCS (2 g, in 10 mL of H$_2$O) and Ru(4,4'-diethoxycarbonyl-4"-nonadecyl-2,2':6',2"-terpyridine)Cl$_3$ complex (0.5 g, in 50 mL of DMF) for 4 h. Then, 20 mL of triethylamine and 10 mL of H$_2$O were added, and the solution was refluxed for a further 24 h to hydrolyze the ester groups on the terpyridine ligand. The solvent volume was reduced on a rotary evaporator to about 10 mL, and than the solution was added to 70 mL of H$_2$O. The resulting precipitate was filtered and dried. The isolated solid was recrystallized from methanol-diethyl ether, after which it was further purified on a Sephadex LH$_2$O column, using methanol as eluent (yield 75%). Anal. $C_{39}H_{49}N_6O_4RuS_3$: Calcd: C, 54.27; H, 5.72; N, 9.74. Found: C, 53.78; H, 5.52; N, 9.64. MS (ESIMS): m/z: 863.20.

(c) Preparation of Ru(4,4'-dicarboxy-4"-nonadecyl-2, 2':6',2"-terpyridine)(NCS)$_3$(TBA)$_2$ This compound was prepared by an analogous procedure to that described in Example 10 (step c). Anal. $C_{71}H_{120}N_8O_4RuS_3$: Calcd: C, 63.31; H, 8.98; N, 8.32. Found: C, 63.31; H, 8.98; N, 8.32. MS (ESIMS): m/z: 1346.76.

EXAMPLE 17

Complex 6a

Preparation of the complex of the formula RuLY$^2$(NCS) (TBA), wherein L is 4,4'-Dicarboxy-4"-nonadecyl-2,2':6',2"-terpyridine (formula 2) and Y$^2$ is 1,1,1-trifluoropentane-2,4-dionato(tfac).

(a) Preparation of Ru(4,4'-diethoxycarbonyl-4"-nonadecyl-2,2':6',2"-terpyridine)Cl$_3$ This compound was prepared by an analogous procedure to that described in Example 9 (step a).

(b) Preparation of Ru(4,4'-dicarboxy-4"-nonadecyl-2,2':6',2"-terpyridine)(tfac)(NCS)

To a solution of the complex Ru(4,4'-diethoxycarbonyl-4"-nonadecyl-2,2':6',2"-terpyridine)Cl$_3$ (300 mg, 0.5 mmol) in methanol (100 mL) was added tfac (236 μL, 2.0 mmol) and Et$_3$N (0.5 mL). The reaction mixture was refluxed for 8 h and the solvent was then allowed to evaporate on a rotary evaporator. The solid mass thus obtained was dissolved in 30 mL of DMF under nitrogen. To this solution was added 5 mL of an aqueous solution of NaSCN (300 mg, 3.7 mmol). After being refluxed for 8 h, 10 mL of Et$_3$N was added, and the solution was refluxed for further 24 h to hydrolyze the ester groups on the terpyridine ligand. The reaction mixture was allowed to cool, and the solvent was removed on a rotary evaporator. The resulting solid was dissolved in 0.1 M aqueous NaOH and Ru(4,4'-dicarboxy-4"-nonadecyl-2,2':6',2"-terpyridine)(tfac)(NCS) was precipitated by the addition of 0.1 M HNO$_3$. The resulting precipitate was filtered and dried. The isolated solid was recrystallized from methanol-diethyl ether, after which it was further purified on a Sephadex LH$_2$O column, using methanol as eluent (yield 75%).

(c) Preparation of Ru(4,4'-dicarboxy-4"-nonadecyl-2,2':6',2"-terpyridine)(tfac)(NCS)(TBA)

This compound was prepared by an analogous procedure to that described in Example 10 (step c).

EXAMPLE 18

Complex 7b

Preparation of the complex of the formula RuLY$^3$(NCS)(TBA), wherein L is 4,4'4"-trimethoxycarbonyl-2,2':6',2"-terpyridine (formula 1) and Y$^3$ is 4,4,4-trifluoro-1-(4-fluorophenyl)butane-1,3-dione (F-phtfac).

(a) Preparation of Ru(4,4'4"-trimethoxycarbonyl-2,2':6',2"-terpyridine)Cl$_3$

This compound was prepared by an analogous procedure to that described in Example 9 (step a).

(b) Preparation of Ru(4,4'-dicarboxy-4"-nonadecyl-2,2':6',2"-terpyridine)(F-phtfac)(NCS)

This compound was prepared by an analogous procedure to that described in Example 17 (step b).

(c) Preparation of Ru(4,4'-dicarboxy-4"-nonadecyl-2,2':6',2"-terpyridine)(F-phtfac)(NCS)(TBA)

This compound was prepared by an analogous procedure to that described in Example 10 (step c).

EXAMPLE 19

Complex 8a

Preparation of the complex of the formula RuLY$^4$(NCS), wherein L is 4,4'-dicarboxy-4"-nonadecyl-2,2':6',2"-terpyridine (formula 2) and Y$^4$ is 2,2'-bipyridine (bpy).

(a) Preparation of Ru(4,4'-diethoxycarbonyl-4"-nonadecyl-2,2':6',2"-terpyridine)Cl$_3$ This compound was prepared by an analogous procedure to that described in Example 9 (step a).

(b) Preparation of Ru(4,4'-dicarboxy-4"-nonadecyl-2,2':6',2"-terpyridine)(bpy)(NCS)

This compound was prepared by an analogous procedure to that described in Example 17 (step b).

EXAMPLE 20

Complex 9a

Preparation of the complex of the formula RuLY$^4$(NCS)(TBA)$_2$, wherein L is 4,4'-dicarboxy-4"-nonadecyl-2,2':6',2"-terpyridine (formula 2) and Y$^4$ is quinoxaline-2,3-dithiolate(qdt).

(a) Preparation of Ru(4,4'-diethoxycarbonyl-4"-nonadecyl-2,2':6',2"-terpyridine)Cl$_3$ This compound was prepared by an analogous procedure to that described in Example 9 (step a).

(b) Preparation of Ru(4,4'-dicarboxy-4"-nonadecyl-2,2':6',2"-terpyridine)(qdt)(NCS)

This compound was prepared by an analogous procedure to that described in Example 17 (step b).

(c) Preparation of Ru(4,4'-dicarboxy-4"-nonadecyl-2,2':6',2"-terpyridine)(qdt)(NCS)(TBA)$_2$ This compound was prepared by an analogous procedure to that described in Example 10 (step c).

EXAMPLE 21

Complex 10a

Preparation of the complex of the formula RuLY$^4$(NCS)(TBA)$_2$, wherein L is 4,4'-dicarboxy-4"-nonadecyl-2,2':6', 2"-terpyridine (formula 2) and Y$^4$ is oxalic acid (ox).

(a) Preparation of Ru(4,4'-diethoxycarbonyl-4"-nonadecyl-2,2':6',2"-terpyridine)Cl$_3$ This compound was prepared by an analogous procedure to that described in Example 9 (step a).

(b) Preparation of Ru(4,4'-dicarboxy-4"-nonadecyl-2,2':6',2"-terpyridine)(ox)(NCS)

This compound was prepared by an analogous procedure to that described in Example 17 (step b).

(c) Preparation of Ru(4,4'-dicarboxy-4"-nonadecyl-2,2':6',2"-terpyridine)(ox)(NCS)(TBA)$_2$ This compound was prepared by an analogous procedure to that described in Example 10 (step c).

EXAMPLE 22

Complex 11a

Preparation of the complex of formula $RuLY^4(NCS)$, wherein L is 4,4'-dicarboxy-4"-nonadecyl-2,2':6',2"-terpyridine (formula 2) and $Y^4$ is ethylenediamine(en).

(a) Preparation of Ru(4,4'-diethoxycarbonyl-4"-nonadecyl-2,2':6',2"-terpyridine)$Cl_3$ This compound was prepared by an analogous procedure to that described in Example 9 (step a).

(b) Preparation of Ru(4,4'-dicarboxy-4"-nonadecyl-2,2':6',2"-terpyridine)(en)(NCS)

This compound was prepared by an analogous procedure to that described in Example 17 (step b).

Preparation of Sensitized Semiconductor Electrode:

Nanocrystalline $TiO_2$ films of about 20 μm were prepared by spreading a viscous dispersion of colloidal $TiO_2$ particles (Sloaronix) on a conducting glass support (Asahi TCO glass, fluorine-doped $SnO_2$ overlayer, transmission>85% in the visible, sheet registance 7-8 ohms/square) with heating under air for 30 min at 500° C. The performance of the film as a sensitized photoanode was improved by further deposition of $TiO_2$ from aqueous $TiCl_4$ solution. A freshly prepared aqueous 0.2 M $TiCl_4$ solution applied onto the electrode. After being left for 20 min at 70° C. in a closed chamber, the electrode was washed with distilled water. Immediately before being dipped into the dye solytion, it was fired again for 30 min at 500° C. in air. After cooling under a continuous argon flow the glass sheet is immediately transferred to a $2\times10^{-4}$ M solution in 1:1 acetonitrile: n-butanol of the tetrabutylammonium salt of ruthenium complex of 7b (example 18), this solution further containing 40 mM of deoxycholic acid as a co-adsorbent. The adsorption of photosensitizer from the dye solution is allowed to continue for 15 hours after that the glass sheet is withdrawn and washed briefly with absolute ethanol. The $TiO_2$ layer on the sheet assumed a black color owing to the photosensitive coating.

Preparation of Solar Cell:

A solar cell (size: 0.25 $cm^2$) was fabricated using the above electrode and a counter electrode, which was a platinum electrode, obtained by vacuum-deposition of platinum on a conductive glass. The platinum layer had a thickness of 20 nm. An electrolyte solution to be placed between the two electrodes was a redox pair of $I—/I_3—$ obtained using 0.5 M 4-tert-butylpyridine, 0.1 M LiI, 0.6M 1,2-dimethyl-3-propyl imidazolium iodide and 0.1 M I2 as solutes and a liquid of acetonitrile.

Operation of Solar Cell:

A potentiostat was used for measuring short-circuit electric current, open circuit voltage and fill factor. Experiments are carried out with a high pressure Xenon lamp equipped with appropriate filters to simulate AM 1.5 solar radiation. The intensity of the light is 100 mW/$cm^2$. The fill factor defined as the maximum electric power output of the cell divided by the product of open circuit voltage and short circuit current.

It was found that the thus constructed solar cell using sensitizer 7b gave a short-circuit electric current of 20 mA/$cm^2$, an open circuit voltage of 0.70 V and a fill factor FF of 0.73 under irradiation of AM 1.5 using solar simulator light (100 mW/$cm^2$).

What is claimed is:

1. A photosensitizing transition metal complex having the general formula (Ia):

$$MLY^1 \qquad (Ia)$$

in which M is a transition metal selected from Ru(II), Os(II), Fe(II), Re(I) and Tc(I);

L is a polypyridine ligand having the general formula (II):

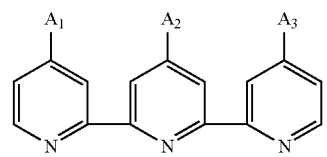

(II)

wherein at least one of $A_1$, $A_2$ and $A_3$ is an anchoring group selected from —COOH, —COON($C_4H_9$)$_4$, —PO(OH)$_2$, —PO(O$R_1$)$_2$ (where $R_1$ is an alkyl group having 1 to 30 carbon atoms), —CO(NHOH), and when there is the remaining $A_1$, $A_2$ and $A_3$ being not said anchoring group, it may be a hydrogen atom, an alkyl group having 1 to 50 carbon atoms, an alkylamide group having 2 to 50 carbon atoms or an aralkyl group having 7 to 50 carbon atoms, and $Y^1$ is a group selected from the formulae (IIIa) to (IIId):

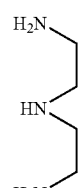

(III a)

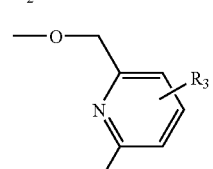

(III b)

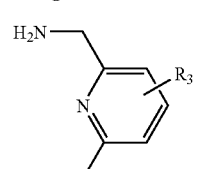

(III c)

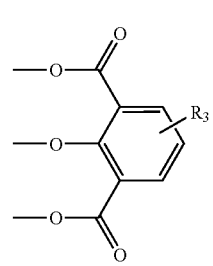

(III d)

where $R_3$ is an alkyl group having 1 to 50 carbon atoms, an alkoxyalkyl group having 2 to 30 carbon atoms, an aminoalkyl group having 1 to 30 carbon atoms, an alkoxycarbonyl group having 2 to 20 carbon atoms, an alkylamide group having 2 to 30 carbon atoms, a cyano group or a hydrogen atom.

2. A photosensitizing transition metal complex of claim 1, which is a complex of the general formula (Ia) in which M is Ru(II) or Os(II);

L is a polypyridine ligand having the subformula (IIa):

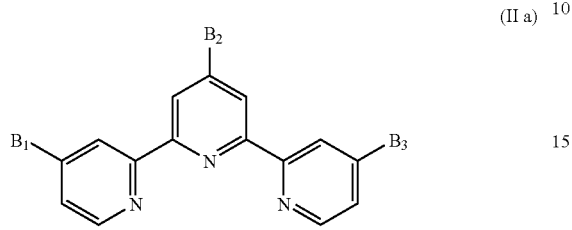

(II a)

where $B_1$, $B_2$ and $B_3$ are H, —COON, —COON($C_4H_9$)$_4$ or —PO(OH)$_2$ provided that at least one of $B_1$, $B_2$ and $B_3$ is different from hydrogen atom; and $R_3$ is an alkyl group having 6 to 30 carbon atoms or a hydrogen atom.

3. A photosensitizing transition metal complex of claim 1, which is a complex of the general formula (Ia) in which M is Ru(II) or Os(II);

L is a polypiridine ligand having the subformula (IIb):

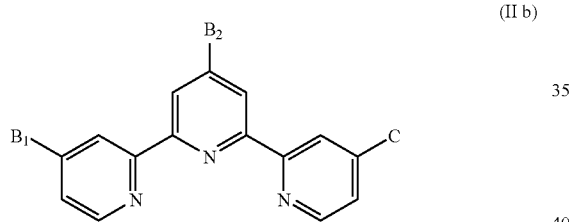

(II b)

where $B_1$ and $B_2$ are, the same or different, a hydrogen atom, —COOH, —COON($C_4H_9$)$_4$, —PO(OH)$_2$, provided that any one of $B_1$ and $B_2$ is different from a hydrogen atom, and C is an alkyl group having 6 to 30 carbon atoms; and $R_3$ is an alkyl group having 6 to 30 carbon atoms or a hydrogen atom.

4. A photovoltaic cell comprising a support, a conductive layer formed on the support, and a porous semiconductor layer formed on the conductive layer, a counter electrode, and an electrolyte deposited there between wherein the porous semiconductor layer carries a photosensitizing transition metal complex as claimed in claim 1.

5. A method of photosensitizing a photovoltaic cell comprising including a photosensitizing transition metal complex having the general formula (Ia) in said photovoltaic cell:

$$MLY^1 \quad (Ia)$$

in which M is a transition metal selected from Ru(II), Os(II), Fe(II), Re(I) and Tc(I);

L is a polypyridine ligand having the general formula (II):

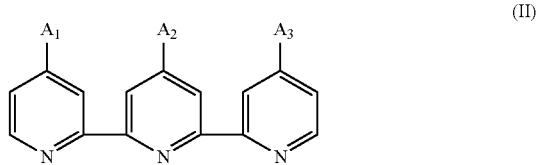

(II)

wherein at least one of $A_1$, $A_2$ and $A_3$ is an anchoring group selected from —COOH, —COON($C_4H_9$)$_4$, —PO(OH)$_2$, —PO(OR$_1$)$_2$ (where $R_1$ is an alkyl group having 1 to 30 carbon atoms), —CO(NHOH), and when there is the remaining $A_1$, $A_2$ and $A_3$ being not said anchoring group, it may be a hydrogen atom, an alkyl group having 1 to 50 carbon atoms, an alkylamide group having 2 to 50 carbon atoms or an aralkyl group having 7 to 50 carbon atoms, and $Y^1$ is a group selected from the formulae (IIIa) to (IIId):

(III a)

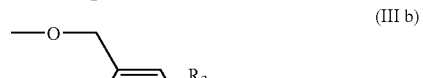

(III b)

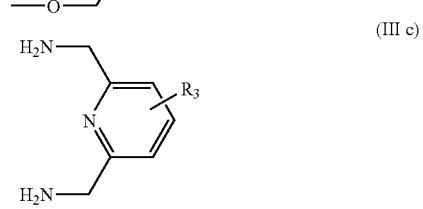

(III c)

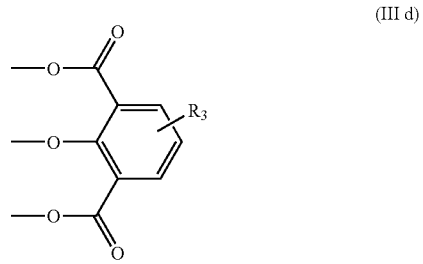

(III d)

where $R_3$ is an alkyl group having 1 to 50 carbon atoms, an alkoxyalkyl group having 2 to 30 carbon atoms, an aminoalkyl group having 1 to 30 carbon atoms, an alkoxycarbonyl group having 2 to 20 carbon atoms, an alkylamide group having 2 to 30 carbon atoms, a cyano group or a hydrogen atom.

* * * * *